(12) United States Patent
Terlecky et al.

(10) Patent No.: US 7,601,366 B2
(45) Date of Patent: Oct. 13, 2009

(54) PROMOTION OF PEROXISOMAL CATALASE FUNCTION IN CELLS

(75) Inventors: Stanley R. Terlecky, Bloomfield Hills, MI (US); Paul A. Walton, London (CA)

(73) Assignee: Wayne State University, Detroit, MI (US)

( * ) Notice: Subject to any disclaimer, the term of this patent is extended or adjusted under 35 U.S.C. 154(b) by 394 days.

(21) Appl. No.: 10/533,124

(22) PCT Filed: Oct. 30, 2003

(86) PCT No.: PCT/US03/34512

§ 371 (c)(1),
(2), (4) Date: Dec. 27, 2005

(87) PCT Pub. No.: WO2004/042011

PCT Pub. Date: May 21, 2004

(65) Prior Publication Data

US 2006/0141598 A1 Jun. 29, 2006

Related U.S. Application Data

(60) Provisional application No. 60/422,100, filed on Oct. 30, 2002.

(51) Int. Cl.
*A61K 9/127* (2006.01)
*A61K 38/44* (2006.01)
*C12N 9/08* (2006.01)

(52) U.S. Cl. .................. 424/450; 424/94.4; 435/192

(58) Field of Classification Search ................ None
See application file for complete search history.

(56) References Cited

U.S. PATENT DOCUMENTS 5,824,469 A * 10/1998 Horwitz et al. ................ 435/6

6,057,136 A * 5/2000 Bower et al. ................ 435/119
6,159,710 A * 12/2000 Fraser et al. ............... 435/69.1

OTHER PUBLICATIONS

Sheik et al. (PNAS 95 : 2961, 1998).*
Trelease, R.N. et al. Rat Liver Catalase is Sorted to Peroxisomes By Its C-Terminal Tripepeptide Ala-Asn-Leu Not By the Internal Ser-Lys-Leu Motif. Eur. J. Cell Biol.71: 248-258. (Nov. 1996).*
Fuijiwara, C. et al. "Catalase-less Peroxisomes". J. Biol. Chem. 275(47): 37271-37277 (Nov. 2000).*
G.Lametschwandtner et al. "The Difference in Recognition of Terminal Tripeptides as Peroxisomal Targeting Signal 1 Between Yeast and Human Is Due to Different Affinities of Their Receptor Pex5p to the Cognate Signal and to Residues Adjacent to It", J. Biol. Chem. vol. 273(50):33635-33643. (Dec. 1998).*

* cited by examiner

*Primary Examiner*—Rebecca Prouty
(74) *Attorney, Agent, or Firm*—Browdy & Neimark, P.L.L.C.

(57) ABSTRACT

The molecular mechanisms of peroxisome biogenesis have begun to emerge: in contrast, relatively little is known about how the organelle functions as cells age. The present inventors characterized age-related changes in peroxisomes of human cells and showed that aging compromises peroxisomal targeting signal 1 (PTS 1) protein import, with the critical antioxidant enzyme, catalase, especially affected. The number and appearance of peroxisomes are altered in these cells, and the organelles accumulate the PTS1-import receptor, Pex5p, on their membranes. Concomitantly, cells produce increasing amounts of the toxic metabolite, $H_2O_2$, and this increased load of reactive oxygen species (ROS) may further reduce peroxisomal protein import and exacerbate the effects of aging. Disclosed are novel compositions and methods for restoring catalase in peroxisomes by use of targeted catalase modified at its C-terminus and/or N-terminus, optionally in combination with polypeptides which promote cellular uptake of proteins, to prevent or overcome the changes that follows aging or that are associated with a number of diseases or disorders.

31 Claims, 11 Drawing Sheets

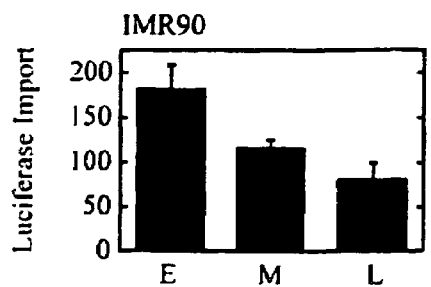
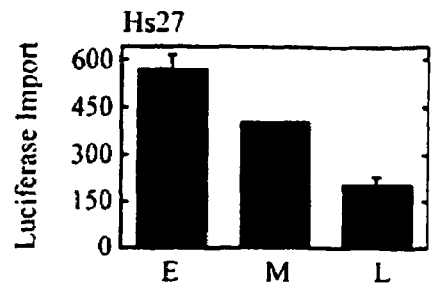
Fig. 1A  Fig. 1B
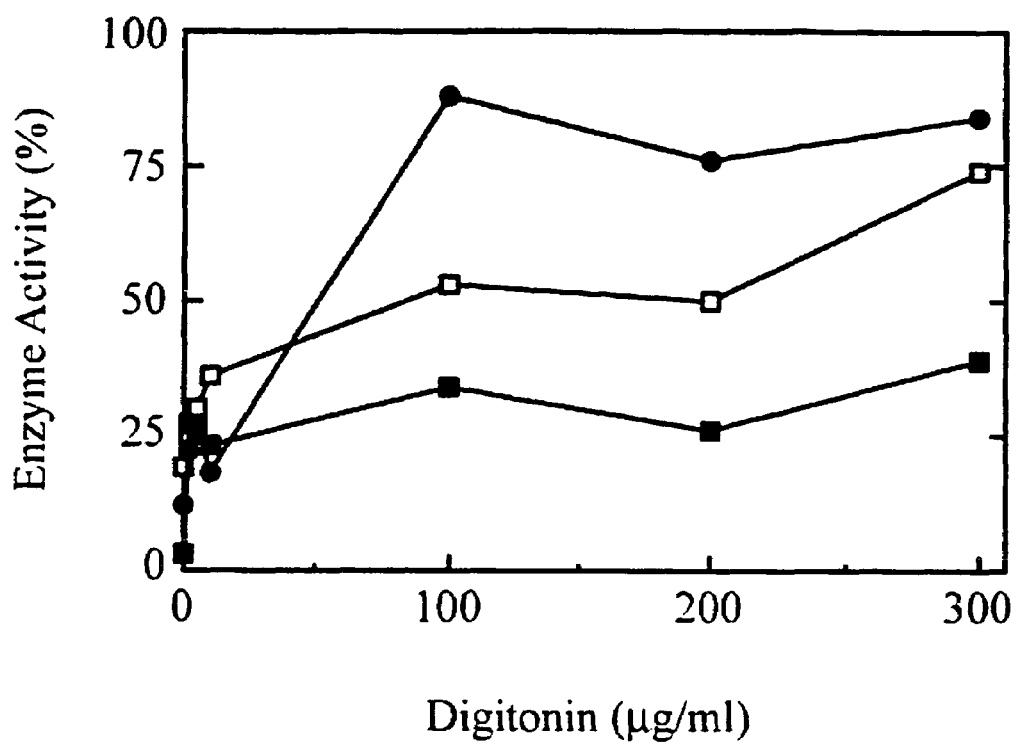
Fig. 2

A
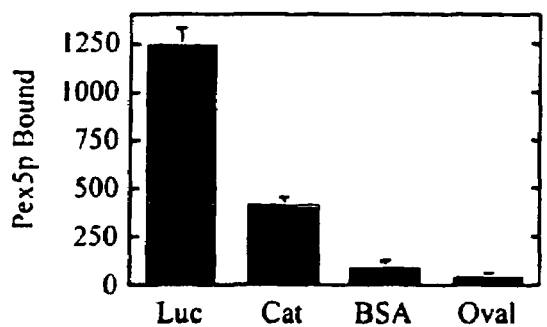
B
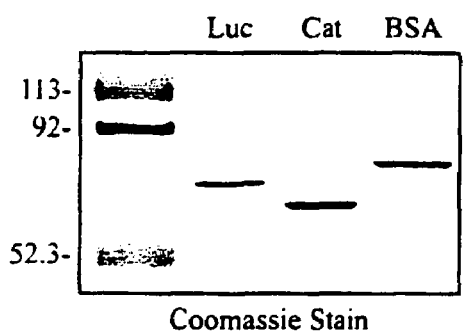 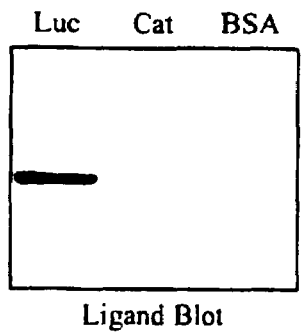
C
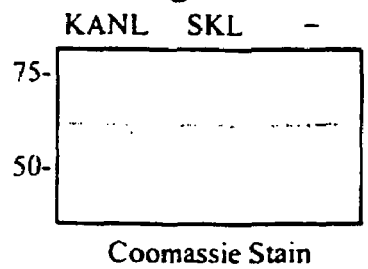 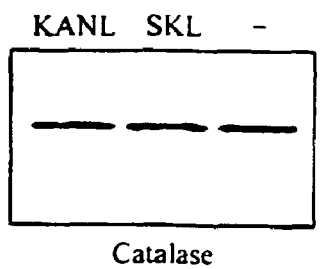 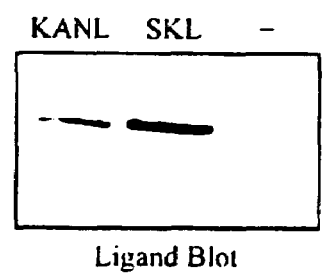

Fig. 4A  Fig. 4B
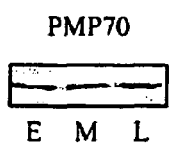
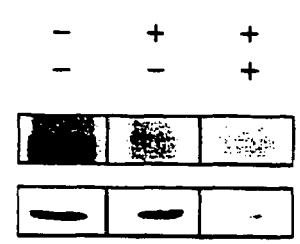
Fig. 4C
Fig. 4E
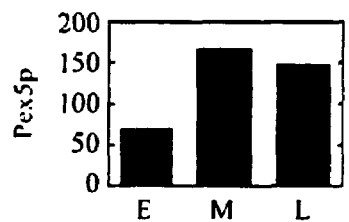
Fig. 4D

SEQUENCE LISTING

<160> NUMBER OF SEQ ID NOS: 21

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 1

Lys Ala Asn Leu
  1

<210> SEQ ID NO 2
<211> LENGTH: 527
<212> TYPE: PRT
<213> ORGANISM: Homo sapiens

<400> SEQUENCE: 2

Met Ala Asp Ser Arg Asp Pro Ala Ser Asp Gln Met Gln His Trp Lys
  1               5                  10                  15

Glu Gln Arg Ala Ala Gln Lys Ala Asp Val Leu Thr Thr Gly Ala Gly
             20                  25                  30

Asn Pro Val Gly Asp Lys Leu Asn Val Ile Thr Val Gly Pro Arg Gly
         35                  40                  45

Pro Leu Leu Val Gln Asp Val Val Phe Thr Asp Glu Met Ala His Phe
 50                  55                  60

Asp Arg Glu Arg Ile Pro Glu Arg Val Val His Ala Lys Gly Ala Gly
 65                  70                  75                  80

Ala Phe Gly Tyr Phe Glu Val Thr His Asp Ile Thr Lys Tyr Ser Lys
                 85                  90                  95

Ala Lys Val Phe Glu His Ile Gly Lys Lys Thr Pro Ile Ala Val Arg
            100                 105                 110

Phe Ser Thr Val Ala Gly Glu Ser Gly Ser Ala Asp Thr Val Arg Asp
        115                 120                 125

Pro Arg Gly Phe Ala Val Lys Phe Tyr Thr Glu Asp Gly Asn Trp Asp
130                 135                 140

Leu Val Gly Asn Asn Thr Pro Ile Phe Phe Ile Arg Asp Pro Ile Leu
145                 150                 155                 160

Phe Pro Ser Phe Ile His Ser Gln Lys Arg Asn Pro Gln Thr His Leu
                165                 170                 175

Lys Asp Pro Asp Met Val Trp Asp Phe Trp Ser Leu Arg Pro Glu Ser
            180                 185                 190

Leu His Gln Val Ser Phe Leu Phe Ser Asp Arg Gly Ile Pro Asp Gly
        195                 200                 205

His Arg His Met Asn Gly Tyr Gly Ser His Thr Phe Lys Leu Val Asn
210                 215                 220

Ala Asn Gly Glu Ala Val Tyr Cys Lys Phe His Tyr Lys Thr Asp Gln
225                 230                 235                 240

Gly Ile Lys Asn Leu Ser Val Glu Asp Ala Ala Arg Leu Ser Gln Glu
                245                 250                 255

Asp Pro Asp Tyr Gly Ile Arg Asp Leu Phe Asn Ala Ile Ala Thr Gly
            260                 265                 270

Lys Tyr Pro Ser Trp Thr Phe Tyr Ile Gln Val Met Thr Phe Asn Gln
        275                 280                 285

```
Ala Glu Thr Phe Pro Phe Asn Pro Phe Asp Leu Thr Lys Val Trp Pro
    290                 295                 300
His Lys Asp Tyr Pro Leu Ile Pro Val Gly Lys Leu Val Leu Asn Arg
305                 310                 315                 320
Asn Pro Val Asn Tyr Phe Ala Glu Val Glu Gln Ile Ala Phe Asp Pro
                325                 330                 335
Ser Asn Met Pro Pro Gly Ile Glu Ala Ser Pro Asp Lys Met Leu Gln
            340                 345                 350
Gly Arg Leu Phe Ala Tyr Pro Asp Thr His Arg His Arg Leu Gly Pro
        355                 360                 365
Asn Tyr Leu His Ile Pro Val Asn Cys Pro Tyr Arg Ala Arg Val Ala
    370                 375                 380
Asn Tyr Gln Arg Asp Gly Pro Met Cys Met Gln Asp Asn Gln Gly Gly
385                 390                 395                 400
Ala Pro Asn Tyr Tyr Pro Asn Ser Phe Gly Ala Pro Glu Gln Gln Pro
                405                 410                 415
Ser Ala Leu Glu His Ser Ile Gln Tyr Ser Gly Glu Val Arg Arg Phe
            420                 425                 430
Asn Thr Ala Asn Asp Asp Asn Val Thr Gln Val Arg Ala Phe Tyr Val
        435                 440                 445
Asn Val Leu Asn Glu Glu Gln Arg Lys Arg Leu Cys Glu Asn Ile Ala
    450                 455                 460
Gly His Leu Lys Asp Ala Gln Ile Phe Ile Gln Lys Lys Ala Val Lys
465                 470                 475                 480
Asn Phe Thr Glu Val His Pro Asp Tyr Gly Ser His Ile Gln Ala Leu
                485                 490                 495
Leu Asp Lys Tyr Asn Ala Glu Lys Pro Lys Asn Ala Ile His Thr Phe
            500                 505                 510
Val Gln Ser Gly Ser His Leu Ala Ala Arg Glu Lys Ala Asn Leu
        515                 520                 525

<210> SEQ ID NO 3
<211> LENGTH: 1586
<212> TYPE: DNA
<213> ORGANISM: Homo sapiens

<400> SEQUENCE: 3
atggctgaca gccgggatcc cgccagcgac cagatgcagc actggaagga gcagcgggcc    60
gcgcagaaag ctgatgtcct gaccactgga gctggtaacc cagtaggaga caaacttaat   120
gttattacag tagggccccg tgggccccctt cttgttcagg atgtggtttt cactgatgaa   180
atggctcatt tgaccgagag agaattcctg agagagttg tgcatgctaa aggagcaggg   240
gcctttggct actttgaggt cacacatgac attaccaaat actccaaggc aaaggtattt   300
gagcatattg aaagaagac tcccatcgca gttcggttct ccactgttgc tggagaatcg   360
ggttcagctg acacagttcg ggaccctcgt gggtttgcag tgaaatttta cacagaagat   420
ggtaactggg atctcgttgg aaataacacc cccatttct tcatcaggga tcccatattg   480
tttccatctt ttatccacag ccaaaagaga atcctcaga cacatctgaa ggatccggac   540
atggtctggg acttctggag cctacgtcct gagtctctgc atcaggtttc tttcttgttc   600
agtgatcggg ggattccaga tggatccatc gccacatgaa tggatatgga tcacatactt   660
tcaagctggt taatgcaaat ggggaggcag tttattgcaa attccattat aagactgacc   720
agggcatcaa aaacctttct gttgaagatg cggcgagact ttcccaggaa gatcctgact   780
```

-continued

```
atggcatccg ggatctttt aacgccattg ccacaggaaa gtaccctcc tggactttt    840 acatccaggt catgacattt aatcaggcag aaacttttcc atttaatcca ttcgatctca    900
ccaaggtttg gcctcacaag gactaccctc tcatcccagt tggtaaactg gtcttaaacc    960
ggaatccagt taattacttt gctgaggttg aacagatagc cttcgaccca agcaacatgc   1020
cacctggcat tgaggccagt cctgacaaaa tgcttcaggg ccgcctttt gcctatcctg   1080 acactcaccg ccatcgcctg ggacccaatt atcttcatat acctgtgaac tgtccctacc   1140
gtgctcgagt ggccaactac cagcgtgatg cccgatgtg catgcaggac aatcagggtg   1200
gtgctccaaa ttactacccc aacagctttg gtgctccgga caacagcct tctgccctgg   1260 agcacagcat ccaatattct ggagaagtgc ggagattcaa cactgccaat gatgataacg   1320
ttactcaggt gcgggcattc tatgtgaacg tgctgaatga ggaacagagg aaacgtctgt   1380
gtgagaacat tgccggccac ctgaaggatg cacaaatttt catccagaag aaagcggtca   1440
agaacttcac tgaggtccac cctgactacg ggagccacat ccaggctctt ctggacaagt   1500
acaatgctga aagcctaag aatgcgattc acacctttgt gcagtccgga tctcacttgg   1560
cggcaaggga gaaggcaaat ctgtga                                       1586
```

<210> SEQ ID NO 4
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 4

Arg Gln Ile Lys Ile Trp Phe Gln Asn Arg Arg Met Lys Trp Lys Lys
 1               5                  10                  15

<210> SEQ ID NO 5
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Arg Gln Ile Lys Ile Phe Phe Gln Asn Arg Arg Met Lys Trp Lys Lys
 1               5                  10                  15

<210> SEQ ID NO 6
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Arg Gln Ile Lys Ile Trp Phe Gln Asn Arg Arg Met Lys Phe Lys Lys
 1               5                  10                  15

<210> SEQ ID NO 7
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

```
<400> SEQUENCE: 7

Arg Gln Ile Lys Ile Phe Phe Gln Asn Arg Arg Met Lys Phe Lys Lys
1               5                   10                  15

<210> SEQ ID NO 8
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Lys Glu Thr Trp Trp Glu Thr Trp Trp Thr Glu Trp Ser Gln Pro Lys
1               5                   10                  15

Lys Lys Arg Lys Val
            20

<210> SEQ ID NO 9
<211> LENGTH: 12
<212> TYPE: PRT
<213> ORGANISM: Artificial Sequence
<220> FEATURE:
<223> OTHER INFORMATION: Description of Artificial Sequence: Synthetic
      motif

<400> SEQUENCE: 9

Lys Glu Thr Trp Trp Glu Thr Trp Trp Thr Glu Trp
1               5                   10

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 10

Lys Lys Lys Arg Lys Val
1               5

<210> SEQ ID NO 11
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 11

Arg Leu Gln Val Val Leu Gly His Leu
1               5

<210> SEQ ID NO 12
<211> LENGTH: 19
<212> TYPE: DNA
<213> ORGANISM: Artificial Sequence
<220> FEATURE:
<223> OTHER INFORMATION: Description of Artificial Sequence: Primer

<400> SEQUENCE: 12
gtgaaccgtc agatccgct                                              19

<210> SEQ ID NO 13
```

-continued

<210> SEQ ID NO 13
<211> LENGTH: 50
<212> TYPE: DNA
<213> ORGANISM: Artificial Sequence
<220> FEATURE:
<223> OTHER INFORMATION: Description of Artificial Sequence: Primer

<400> SEQUENCE: 13
cgtctcgagt tatagatcag ctttcagctc gtccatgccg agagtgatcc        50

<210> SEQ ID NO 14
<211> LENGTH: 30
<212> TYPE: DNA
<213> ORGANISM: Artificial Sequence
<220> FEATURE:
<223> OTHER INFORMATION: Description of Artificial Sequence: Primer

<400> SEQUENCE: 14
ccgctagcgc taccggtcgc caccatggcc        30

<210> SEQ ID NO 15
<211> LENGTH: 42
<212> TYPE: DNA
<213> ORGANISM: Artificial Sequence
<220> FEATURE:
<223> OTHER INFORMATION: Description of Artificial Sequence: Primer

<400> SEQUENCE: 15
cgtctcgagt tataatttgg acaggaacag gtggtggcgg cc        42

<210> SEQ ID NO 16
<211> LENGTH: 31
<212> TYPE: DNA
<213> ORGANISM: Artificial Sequence
<220> FEATURE:
<223> OTHER INFORMATION: Description of Artificial Sequence: Primer

<400> SEQUENCE: 16
acgcaggcct gctgacacgc gggatcccgc c        31

<210> SEQ ID NO 17
<211> LENGTH: 33
<212> TYPE: DNA
<213> ORGANISM: Artificial Sequence
<220> FEATURE:
<223> OTHER INFORMATION: Description of Artificial Sequence: Primer

<400> SEQUENCE: 17
gggcgcaagc tttcacagat ttgccttctc cct        33

<210> SEQ ID NO 18
<211> LENGTH: 44
<212> TYPE: DNA
<213> ORGANISM: Artificial Sequence
<220> FEATURE:
<223> OTHER INFORMATION: Description of Artificial Sequence: Primer

<400> SEQUENCE: 18
gggcgcaagc tttcacagtt tcgatttctc ccttgccgcc aagt        44

<210> SEQ ID NO 19
<211> LENGTH: 32
<212> TYPE: DNA
<213> ORGANISM: Artificial Sequence
<220> FEATURE:
<223> OTHER INFORMATION: Description of Artificial Sequence: Primer

<400> SEQUENCE: 19

```
ggcgcaagct tcactccct tgccgccaag tg                                    32
```

```
<210> SEQ ID NO 20
<211> LENGTH: 6
<212> TYPE: PRT
<213> ORGANISM: Artificial Sequence
<220> FEATURE:
<223> OTHER INFORMATION: Description of Artificial Sequence: Synthetic
      6X-His tag

<400> SEQUENCE: 20

His His His His His His
  1               5

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Lys Ala Asn Leu Ser Leu Leu
  1               5
```

PROMOTION OF PEROXISOMAL CATALASE FUNCTION IN CELLS

This application is a 371 national phase of international application PCT/US03/34512, filed Oct. 30, 2003, which claims the benefit of U.S. provisional application 60/422,100, filed Oct. 30, 2002.

BACKGROUND OF THE INVENTION

1. Field of the Invention

The present invention in the field of biochemistry and medicine is directed to modified catalase proteins designed for increased import into peroxisomes and combinations of these with polypeptides that enhance cellular delivery and uptake of proteins. These compositions are used to treat conditions, such as diseases and disorders associated with aging or with peroxisome deficiency and resultant excesses of hydrogen peroxide and other reactive oxygen species.

2. Description of the Background Art

Peroxisomes are essential subcellular organelles of eukaryotic cells. These multifunctional structures arise through the carefully orchestrated reactions of some two dozen proteins, called peroxins (Terlecky and Fransen, 2000). These are critical processes; defects leave cells either devoid of peroxisomes, or with organelles rendered unable to carry out the myriad of biochemical and metabolic functions ascribed to them. Often, such failings result in disease (Gould and Valle, 2000).

Despite major recent advances in an understanding of how the peroxisome arises and functions, only scant information is available regarding the relationship of the organelle and cellular aging. It is unclear, for example, how the organelle functions as cells age, and what role, if any, the peroxisome plays in the aging process.

The present inventors used, as their model system, human diploid fibroblasts (HDFs)—cells with a finite replicative lifespan. These somatic cells divide (or double) in culture until they reach a limit referred to as the "Hayflick number" (Hayflick, 1965). At this point, their cell-cycle arrests, and they are termed "senescent." This process of cellular senescence occurs in aged whole organisms as well (Dimri et al., 1995). Contributing factors to cellular senescence include telomere shortening, DNA damage and related genomic instability, modified gene expression, and the accumulation of reactive oxygen species (ROS) (reviewed in Johnson et al., 1999). With respect to the latter, mitochondria are widely regarded as the chief cellular generators of ROS, and ironically, a major focus of free radical assault (Lee and Wei, 2001; Beckman and Ames, 1998). However, mitochondria are not the only source of cellular ROS.

Another ROS source are the peroxisomes which house, among their constituent enzymes, a variety of hydrogen peroxide ($H_2O_2$)-generating oxidases. These organelles also contain catalase, which decomposes $H_2O_2$ to water and oxygen and, presumably, prevents accumulation of this toxic compound. Thus, the peroxisome maintains a delicate balance with respect to the relative concentrations or activities of these enzymes to ensure no net production of ROS. How the organelle maintains this equilibrium is unclear, though it is known that peroxisomal pro- and anti-oxidants are tightly coupled, and, under normal conditions, no net accumulation of ROS occurs. It is also not known what happens to these regulatory mechanisms as cells (and organisms) age.

Proteins are directed to the peroxisome by specific peptide sequences, called peroxisomal targeting signals (PTSs), which are recognized by receptor molecules. All but a select few human peroxisomal proteins contain PTS1, a carboxy-terminal sequence (Subramani, 1998). PTS1 is identified and shuttled to the peroxisome by the soluble peroxin, Pex5p (Dammai and Subramani, 2001). For the majority of peroxisomal enzymes, PTS1 is a tripeptide consisting of Ser-Lys-Leu (=SKL) or a closely related variant (Subramani, 1998). In contrast, catalase's PTS1 is a non-canonical PTS1, consisting of the four amino acids, Lys-Ala-Asn-Leu (=KANL)) SEQ ID NO: 1) (Purdue and Lazarow, 1996).

As disclosed herein, according to the present invention, these distinct PTS1s lead to dissimilar recognition by Pex5p, with SKL being a far better substrate than KANL, and, in aging cells, to significantly different import efficiencies. As disclosed herein, aging fibroblasts produce increasing amounts of ROS as an apparent consequence of this uncoupling of peroxisomal pro- and antioxidants. Finally, the present characterization of peroxisomes in aging cells reveals changes in the size and number of these organelles, as well as in their ability to cycle Pex5p from their surfaces and permit its return to the cytosol.

F. G. Sheikh et al., *Proc. Natl. Acad. Sci. USA* 95:2961-2966, 1998) described human cells which did not import catalase efficiently which were derived from an individual with severe neuropathology. In an effort to restore peroxisomal catalase in these cells, the investigators altered the targeting signal of the enzyme. However, the protein was reintroduced by transient transfection with the corresponding gene. Although this strategy corrected the cells' inability to import catalase, this document provided no detailed analysis of why the approach worked. Moreover, transfection of cells and accompanying (drug) selection for stable transformants is clearly not compatible with the therapeutic approaches of the present invention. Upon inspection of the oligonucleotides used in this study, it is possible to conclude that the genetic constructs produced in this study would encode a catalase protein having at its C terminus the sequence KANL-SLL, not even the -SKL tripeptide terminus that the authors ostensibly sought to append to the C-terminus of catalase. Moreover, this study focused solely on restoring catalase in a cell line of one particular patient—but did not disclose what the present inventors have discovered and disclose here for the first time: similar mistargeting of catalase occurs in aging human cells. Obviously, then, the Sheikh et al. document did not even suggest the notion of treating cells prophylactically to slow down aging processes nor the replacement of the native KANL C-terminus of human catalase with the sequences disclosed herein.

L. H. Jin et al., *Free Radic Biol Med* 31 1509-1519, 2001, disclosed that catalase may be introduced into human cells using "protein transduction domains" (PTDs) which are specialized peptide sequences. However, the Jin et al. transduction methodology was not state-of-the-art. A recombinant fusion protein was created, in which the PTD was fulsed directly to the N-terminus of catalase. The fusion protein was expressed, purified under denaturing conditions, and then added to cells. Given these conditions, the denatured catalase that entered the cells had to refold to its active form. Although the document provides evidence that the enzyme entered cells and processed some ROS, there was no evidence suggesting that the molecule was delivered to the peroxisome—its "correct" intracellular address. Indeed, to the contrary, the findings suggested cytosolic accumulation of the enzyme.

The Jin et al. study lacks any description of the presence, in the primary structure of catalase (or catalase fusion protein) of a strong peroxisomal targeting signal. It should also be noted that others have developed protein transduction domains that permit delivery of proteins without requiring denaturation and, perhaps more importantly, without requiring in-frame fusions with the molecule of interest. The present invention is also directed to such molecules.

Morris et al., *Nature Biotechnology*, 19:1173-1176, 2001, described a protein transduction approach which effectively introduces a protein of interest in its native state. The "carrier" simply dissociates from its ligand once having entered the cell, and no longer appears as part of the equation. The present inventors have conceived of combining this technology with a reengineered catalase molecule as the basis of certain embodiments of this invention.

SUMMARY OF THE INVENTION

The present inventors have designed a new, modified catalase molecule which is used in a new process of promoting catalase function in (e.g., restoring it to) defective peroxisomes. The composition comprises an engineered derivative of the critical anti-oxidant enzyme, catalase. The inventors have also discovered that as human cells age, their ability to correctly compartmentalize catalase in peroxisomes is compromised. Other enzymes, namely peroxisomal oxidases, are also imported less efficiently as cells age, but do not appear to be affected to the degree that catalase is. This is believed to be due to the nature of the PTSs on the two classes of protein. The peroxisomal oxidases continue to produce $H_2O_2$ and other ROS, and, because of the reduced levels of catalase, those toxic metabolites accumulate. The build-up of ROS in human cells is thought to be a significant contributor to the aging process and to a number of diseases, particularly degenerative disease that include the neurodegenerative diseases Parkinson's disease, Alzheimer's disease, amyotrophic lateral sclerosis, etc.

Thus, the present invention is directed to compositions and methods for promoting (e.g., restoring) peroxisomal catalase in active form in animal cells, preferably mammalian cells, most preferably human cells—with the goal of reducing the accumulation of ROS inside this organelle, and thereby, inside the cell. This reduction is predicted to increase the life span of such cells—and/or in some other manner to reduce the effects of aging, as well as preventing or possibly reversing degenerative changes that follow prolonged oxidative stress.

Based on the new understanding of the molecular mechanisms of peroxisomal protein import, it is now possible to efficiently direct an enzyme to the organelle under most conditions. One basis for this improved targeting efficiency is use of an altered PTS on the catalase molecule, which permits a higher affinity interaction with a peroxisomal protein import receptor protein, Pex5p. The examples below show that catalase with an altered PTS interacts more efficiently with this Pex5p than does native catalases.

In one embodiment, the present invention combines the technology of catalase "protein therapy" with the ability to "transduce" or deliver the enzyme into human cells, using the protein biochemistry that creates a high affinity ligand for the peroxisomal protein import machinery.

This invention responds to a long unmet need-replacement of biological deficiency. The studies described herein clearly demonstrate that human cells are less able to correctly compartmentalize catalase as they age. Concomitantly, these cells produce elevated levels of ROS. Using their skill in the arts of protein trafficking, cell biology, and protein biochemistry, the present inventors describe a strategy—and, by extension, compounds, by which to reverse this catalase deficiency and reduce or perhaps eliminate the cellular accumulation of ROS.

Sheikh and colleagues (supra) disclosed that catalase mistargeting in human cells is associated with a "severe neurological disorder." Therefore, the development of the present catalase technology impacts human health, disease, and aging.

The present results suggest that introduction of catalase into human cells without modifying its targeting signal will result in the enzyme accumulating largely in the cytosol. There, the enzyme is dilute, distant to the site of ROS production, and subject to modification, inactivation or degradation. However, as has been demonstrated in lower organisms (e.g., worms, flies), even increased cytosolic levels of catalase can have dramatic effects on life-span.

In some embodiments, the present invention refocuses two technologies. The first involves introduction of a critically important anti-oxidant enzyme into human cells, termed "delivery." The second aims to correctly compartmentalize the enzyme in the organelle where it normally resides and is known to function most effectively. This is termed "targeting."

Few methods are currently available to introduce (genes and) proteins into cells. One method with great promise has been broadly termed "gene therapy."

Although it might be possible to provide catalase to cells extracellularly and allow the enzyme to quench ROS from there, such an approach does not appear to be the most efficient strategy (even though provision of catalase in such manner might indeed process some ROS).

BRIEF DESCRIPTION OF THE DRAWINGS

FIG. 1 is a series of graphs showing PTS1(-SKL)-protein import in early, middle, and late passage human diploid fibroblasts (HDFs). FIG. 1A: Semi-intact IMR90 HDFs were incubated at 37° C. with biotinylated luciferase in an in vitro import reaction. After 45 min, the cells were centrifuged, homogenized, and an organelle pellet/peroxisome fraction prepared. The level of import in equivalent portions of the organelle pellets was determined by ELISA. Values presented (means and ranges of duplicate samples) are absorbance units at 490 nm with time zero values subtracted. E=early passage cells, M=middle passage cells, and L=late passage cells. FIG. 1B: Semi-intact Hs27 HDFs were incubated with biotinylated luciferase as in FIG. 1A except that import was assayed directly in cells.

FIG. 2 is a graph showing catalase latency. IMR90 HDFs were treated with increasing concentrations of digitonin, and the levels of catalase (■) and lactate dehydrogenase (●) were determined. Data are presented as % of total cellular activity (set at 100) which was determined in the presence of 1% Triton X-100. Solid symbols=early passage cells; open symbols=late passage cells.

FIG. 3 is a graph and series of blots showing an analysis of Pex5p binding in a solid phase assay. FIG. 3A: 2 μg of luciferase (Luc), catalase (Cat), bovine serum albumin (BSA), or ovalbumin (Oval) were coated onto microtiter wells, and the binding of GST-Pex5p was examined. Values shown (absorbance units at 490 nm) represent the mean±SD (n=5). Ligand blot assays are shown in FIGS. 3B through 3F. 800 ng of Luc, Cat, or BSA were separated by SDS-PAGE and either stained with Coomassie blue (FIG. 3B) or transferred to nitrocellulose membranes and blotted with GST-Pex5p (FIG. 3C). FIGS. 3D, 3E and 3F: 200 ng of recombinant human catalase containing its own PTS1 (KANL), an altered PTS1 (SKL), or no PTS1 (–), were separated by SDS-PAGE and either stained with Coomassie blue (FIG.

3D) or transferred to nitrocellulose membranes and immunoblotted with anti-catalase antisera (FIG. 3E) or blotted with GST-Pex5p (FIG. 3F).

FIG. 4 is a series of blots and a graph showing the association of Pex5p with organelle membranes. FIGS. 4A through 4C show that Pex5p accumulates on organelles of aging HDFs. Pex5p was immunoprecipitated from detergent solubilized organelles of early passage (E), middle passage (M), or late passage (L) IMR90 HDFs using anti-Pex5p antisera (α5), or preimmune sera (PI), as indicated, and immunoblotted with anti-Pex5p antisera. Organellar PMP70 was also examined by immunoblotting. FIG. 4D shows quantification of the α5 immunoblot with a Fujifilm LAS100plus luminescent image analyzer. The units on the ordinate are arbitrary. Equivalent results were obtained in three different experiments. FIG. 4E shows that Pex5p accumulates on the outside of organelles from late passage cells. Organelles from late passage IMR90 HDFs were treated or not with proteinase K and Triton X-100, as indicated, and the resultant organelles immunoblotted with anti-Pex5p or anti-catalase antisera.

Figure 5:
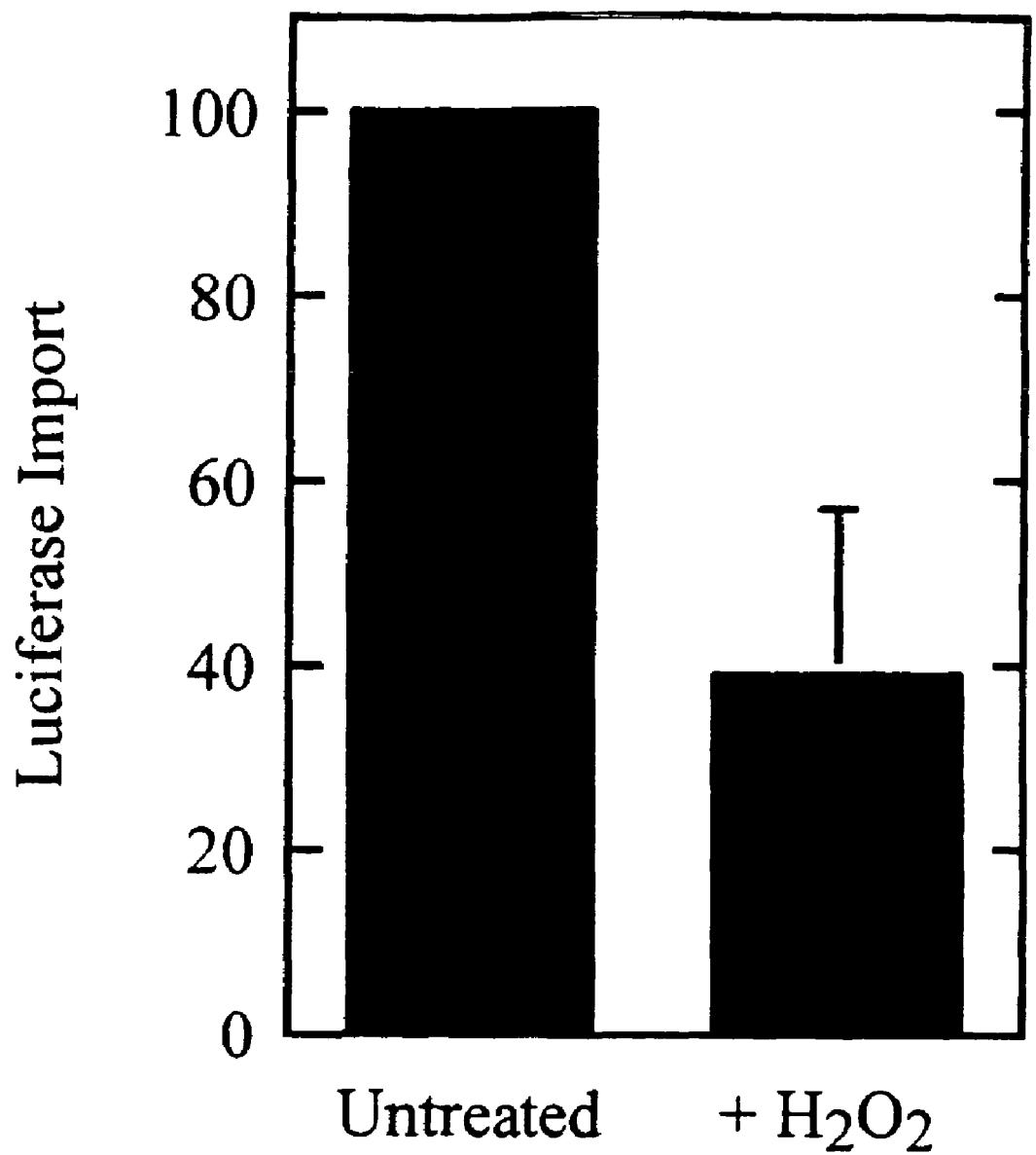

FIG. 5 is a graph showing that $H_2O_2$ which accumulates in aging HDFs inhibits peroxisomal protein import. Early passage IMR90 HDFs were pretreated with $H_2O_2$ and peroxisomal import was examined as in FIG. 1A. Results (mean±SD) are pooled from five experiments and normalized to the untreated control value (arbitrarily set at 100) to permit comparison.

Figure 6:
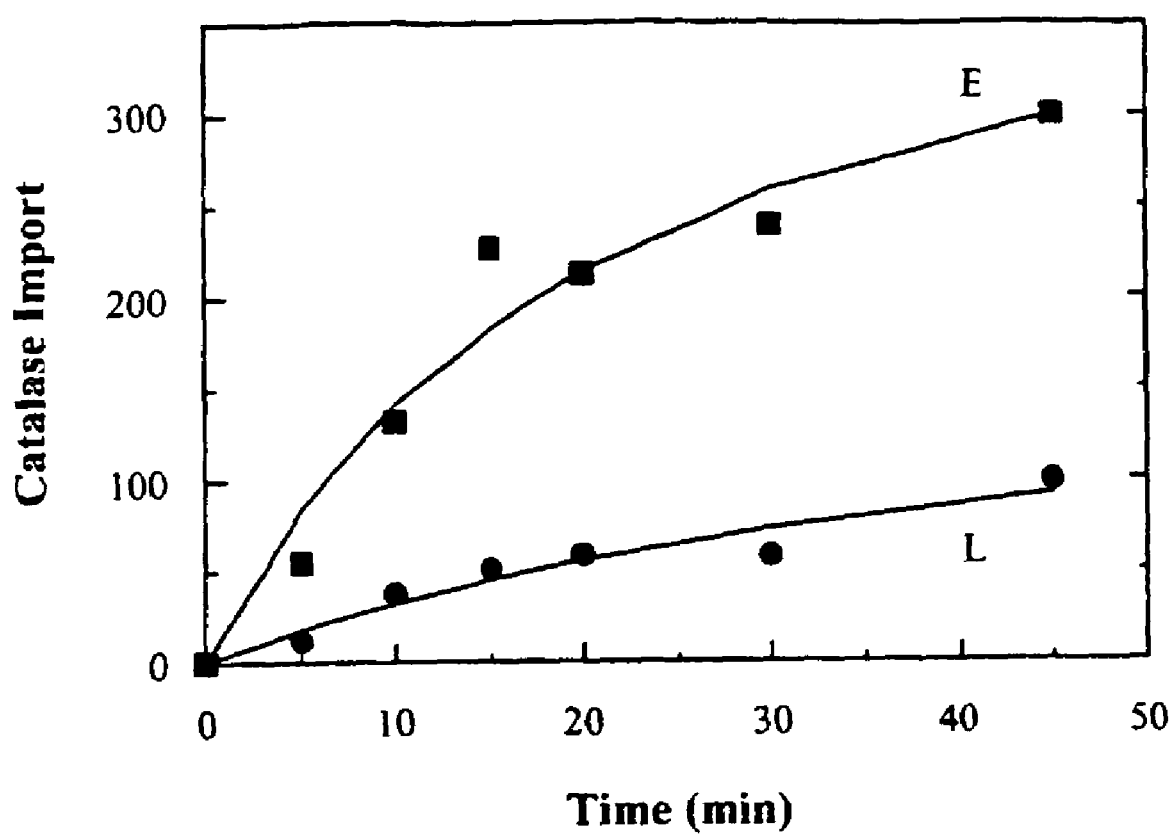

FIG. 6 shows catalase import in early (E) and late (L) passage human diploid fibroblasts. Peroxisomal import of biotinylated catalase was examined as described (Terlecky et al. (2001), *Exp. Cell Res.* 263, 98-106) in a reaction normalized to cell number as outlined in Legakis et al. (2002) *Mol. Biol. Cell.* 13, 4243-4255.

Figure 7:
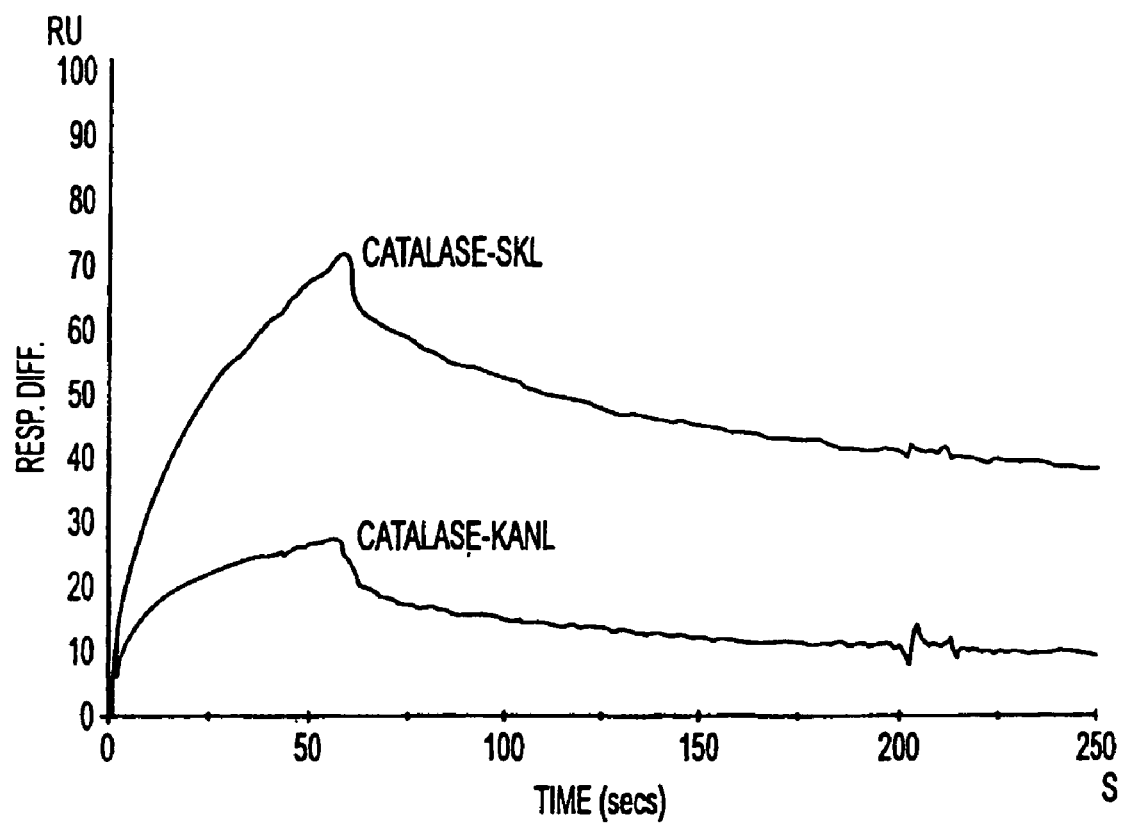

FIG. 7 shows binding of Pex5p to catalase derivatives. Surface plasmon resonance was used to examine binding of Pex5p to catalase with its own PTS (Catalase-KANL) as well as with an altered PTS (Catalase-SKL). Note that the results presented are response units (RU) and have been corrected for non-specific binding to a control surface. 1000 response units of GST-tagged Pex5p was coupled to a CM5 sensor chip surface by amine coupling according to BIACORE's protocol. 10 uM of the catalase constructs were injected over the chip surface at 10 uL/min for 1 min. A BIACORE biosensor 3000 was used in all experiments.

Figure 8:
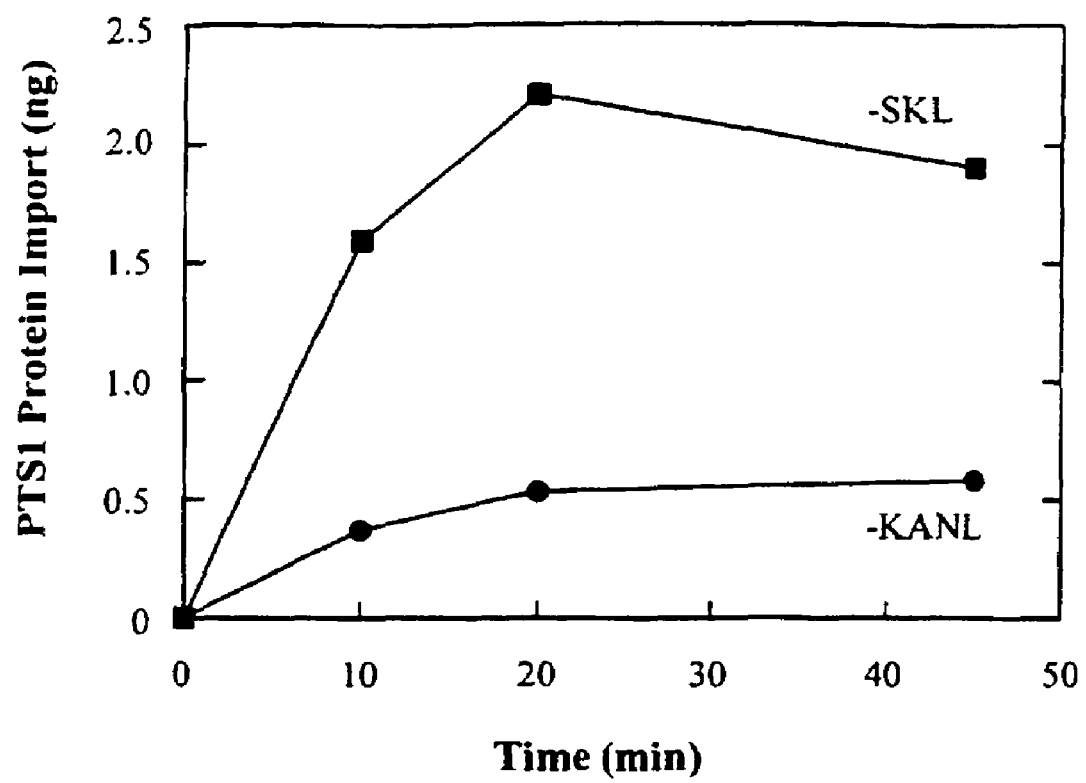

FIG. 8 shows quantitative analysis of peroxisomal protein import: a comparison of luciferase (-SKL) and catalase (-KANL) import into human diploid fibroblasts. Peroxisomal import of biotinlylated luciferase and catalase was measured at various times by an ELISA-based quantitative assay as previously described (Terlecky et al. (2001), *Exp. Cell Res.* 263, 98-106.

Figure 9:
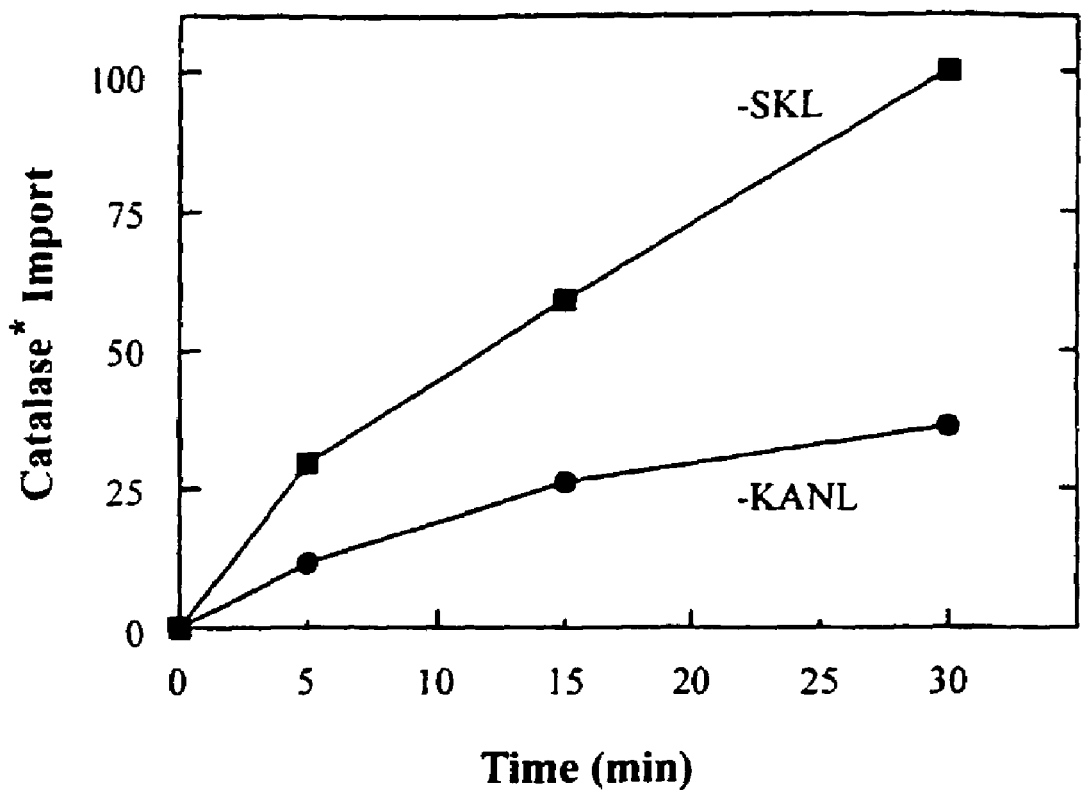

FIG. 9 shows peroxisomal import of catalase derivatives: a comparison of catalase-SKL (-SKL) and catalase-KANL (-KANL) import into peroxisomes of human cells. Peroxisomal import of biotinlylated catalase derivatives was measured at various times by an ELISA-based quantitative assay as previously described (Terlecky et al. (2001), *Exp. Cell Res.* 2632, 98-106).

Figure 10:
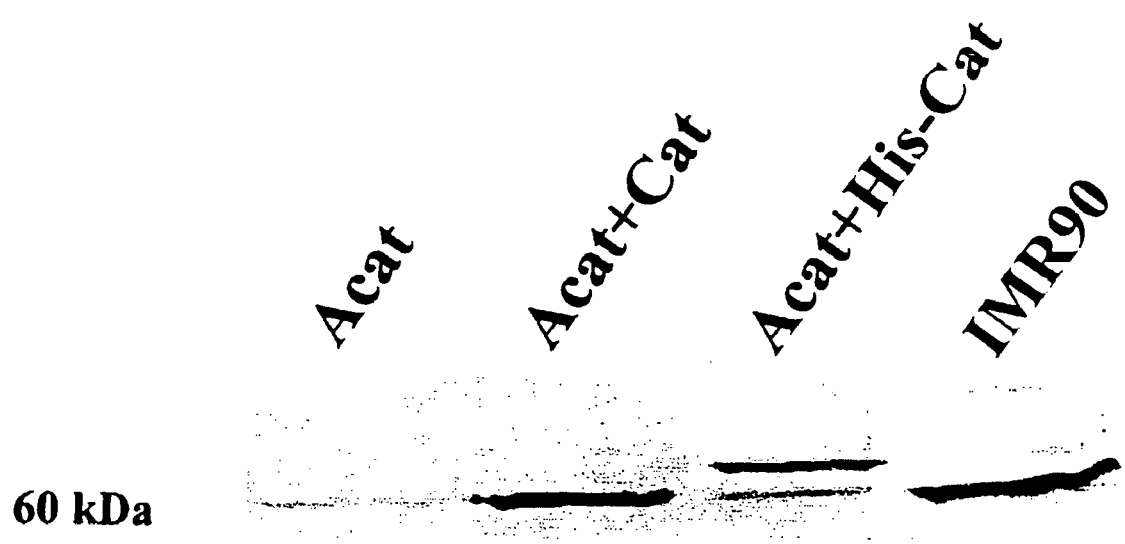

FIG. 10 shows the transduction of catalase. Western blots were generated of acatalasemia cells (Acat), IMR90 cells (IMR90), or acatalasemia cells transduced with human catalase (Acat+Cat) or His-tagged catalase (Acat+His–Cat). (Anti-human catalase antibodies were used in the primary incubation. Note: catalase monomers migrate at 60 kDa on SDS-PAGE.)

Figure 11:
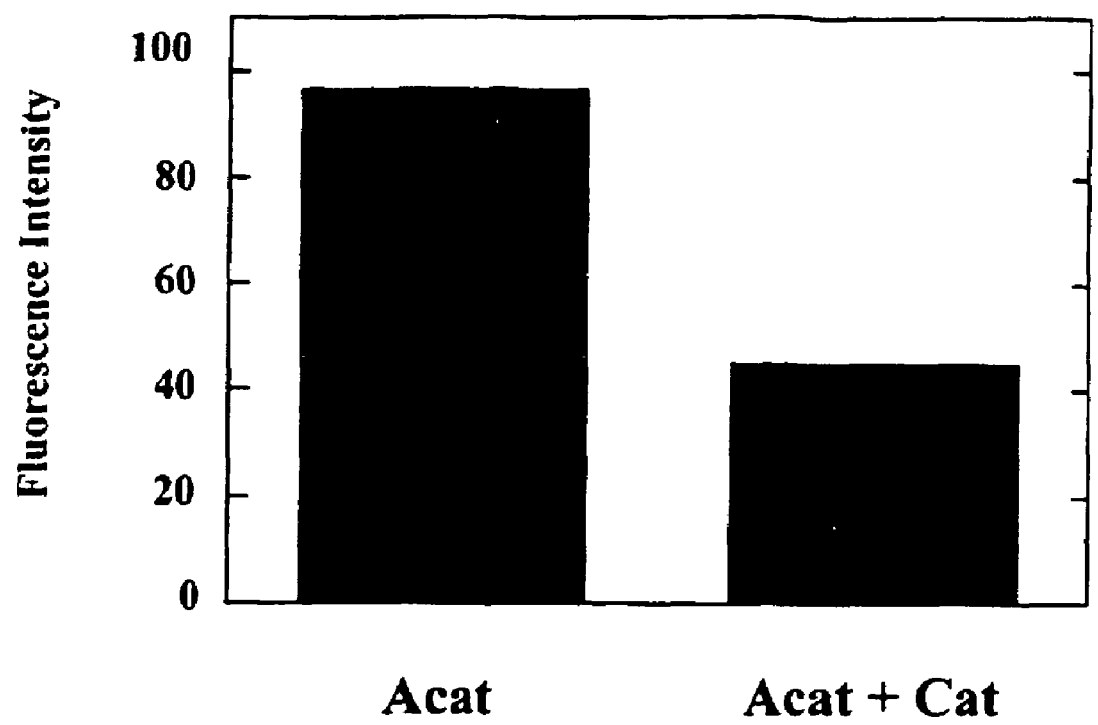

FIG. 11 shows an analysis of cellular hydrogen peroxide ($H_2O_2$) levels. Human acatalasemia (Acat), and acatalasemia cells transduced with catalase (Acat+Cat) were examined for the presence of $H_2O_2$ using the fluorescent dye 2',7'-dichlorofluorescein diacetate. Quantitative analysis of accumulated cellular fluorescence was performed using National Institutes of Health's Image J Software. Note that the results presented show a decrease of approximately 60% in the level of $H_2O_2$ in catalase treated cells.

Figure 12:
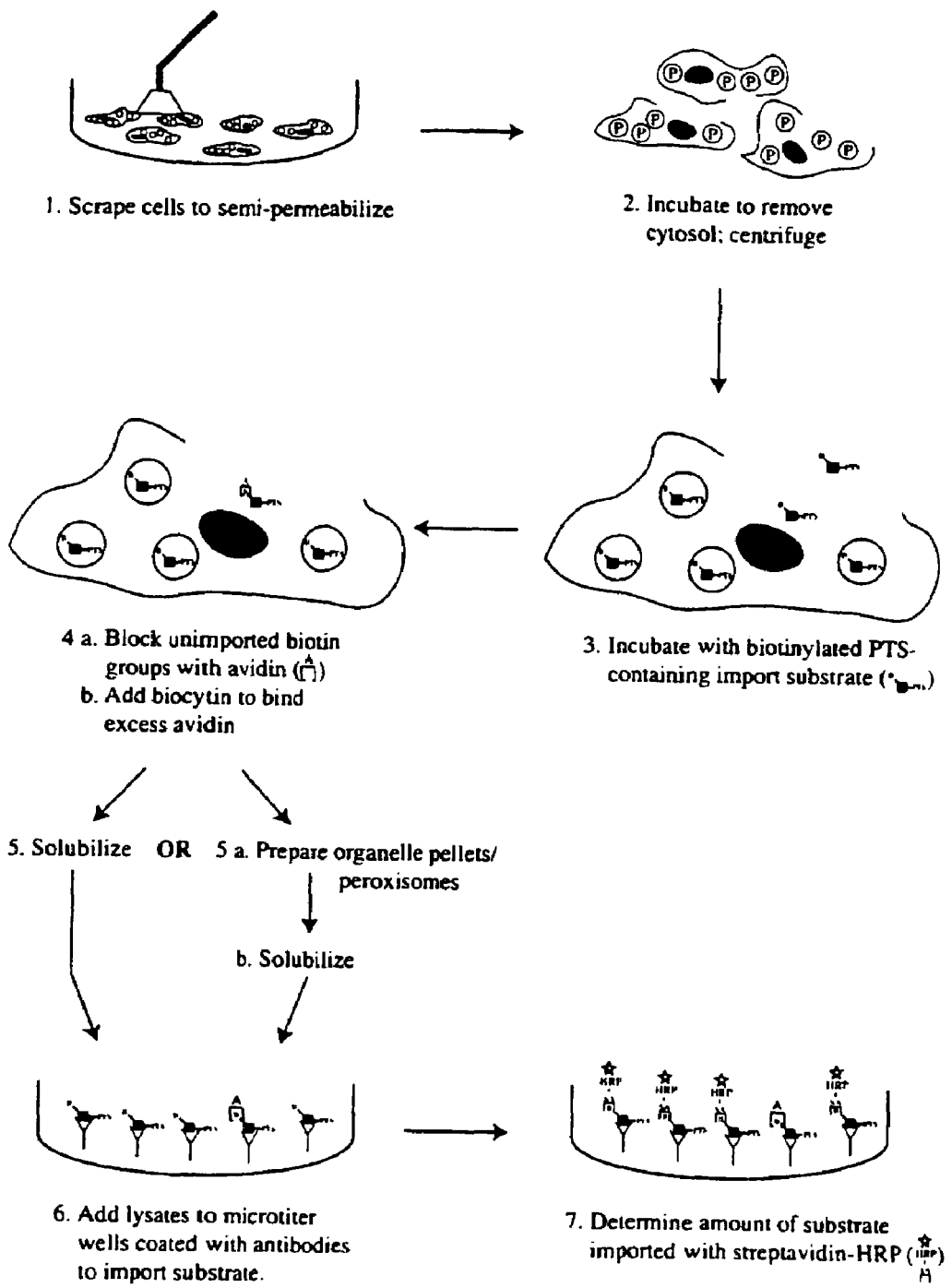

FIG. 12 shows schematically a quantitative in vitro assay for peroxisomal protein import. The assay is ELISA-based and employs semi-permeabilized human cells and a biotinylated import substrate. In the "basic protocol," mport is assessed directly in cells. In an "alternate protocol," import is quantitated after isolation of cellular organelles/peroxisomes. A, avidin; B, biotin; HRP, horseradish peroxidase; P, peroxisome; PTS, peroxisomal targeting signal; SA, streptavidin.

DESCRIPTION OF THE PREFERRED EMBODIMENTS

The present disclosure makes clear that certain cells (including aging human cells) fail to efficiently import their peroxisomal enzymes, including catalase. Catalase contains a particularly "weak" targeting signal, the KANL C-terminal tetrapeptide. The present invention is based in part upon the notion that catalase engineered to contain a "strong" targeting signal such as -SKL or functional derivatives of SKL will reduce, or perhaps even reverse, cellular accumulation (e.g., age-related cellular accumulation) of highly toxic reactive oxygen species (ROS). Such catalases are referred to herein as "modified" or "targeted" catalases.

Thus, in a preferred modified catalase, the KANL sequence has been removed and substituted with SKL or a functional variant thereof (See Examples). Any variant of the tripeptide SKL can be used in this invention provided that this variant binds to Pex5p with sufficient, but not too high, affinity so that it permits efficient import and release of catalase into peroxisomes and, thereby, to decomposition of $H_2O_2$ generated in the peroxisomes. In one embodiment, the tripeptide is not SLL. In general, it is preferred that the tripeptide not be preceded by KANL.

In a preferred SKL variant at least one amino acid residue and preferably, only one, is substituted by a different residue. For a detailed description of protein chemistry and structure, see, for example, Schulz, G. E. et al., *Principles of Protein Structure*, Springer-Verlag, New York, 1979, and Creighton, T. E., *Proteins: Structure and Molecular Principles*, W.H. Freeman & Co., San Francisco, 1984, which are hereby incorporated by reference. The types of substitutions that may be made in the amino acid sequence may be based on analysis of the frequencies of amino acid changes between a homologous protein of different species. Based on such an analysis, conservative substitutions include exchanges such as the following:

| 1 | Small aliphatic, nonpolar or slightly polar residues | Ala, Ser, Thr (Pro, Gly) (A, S, T (P, G)); |
|---|---|---|
| 2 | Polar, negatively charged residues and their amides | Asp, Asn, Glu, Gln; (D, N, E, Q) |
| 3 | Polar, positively charged residues | His, Arg, Lys; (H, R, K) |
| 4 | Large aliphatic, nonpolar residues | Met, Leu, Ile, Val (Cys); M, L, I, V (C) |
| 5 | Large aromatic residues | Phe, Tyr, Trp. (F, Y, W) |

Most substitutions according to the present invention are those that do not produce changes in the functional characteristics of the peptide molecule, viewed primarily as its action as a PTS1. Even when it is difficult to predict the exact effect of a substitution in advance of doing so, one skilled in the art will appreciate that the effect can be evaluated by routine screening assays, preferably the biological and biochemical assays herein. The substituting amino acids may be naturally-occurring or non naturally-occurring amino acids or amino acid derivatives.

Preferred substitution variants have conservative substitutions of any one or more of S, K, and L. Preferred substitutions include:

(1) A, G, C or T (preferably A or C) in place of S in the N-terminal "−3" position;

(2) R or H in place of K in the second (−2) position;

(3) I, V or M (preferably M) in place of L in the third (−1) position.

Any combination of the above types of substitutions is acceptable. One preferred substitution variant is AKL, which is a known C-terminal sequence in several peroxisomal enzymes and an effective PTS1. Interestingly, a targeted catalase can be prepared by making only a single amino acid substitution in the native catalase sequence, where the three C-terminal residues are ANL. The substitution of a Lys (K) for the Asn (N) results in the catalase terminating with an AKL peptide that will confer a strong peroxisomal import signal on the enzyme.

Also included in the invention are addition variants in which one or two residues are added at the N-terminal side of SKL or its substitution variant. Again, any such addition is contemplated provided that it does not interfere with the peroxisomal import-enhancing function of this peptide structure.

For a discussion of variants that can serve as functional PTSs, see Lametschwandtner et al. (1998) *J. Biol. Chem.* 273, 33635-33643 and Gotto et al. (2003) *J. Biochem.* 42, 1660-1666.

The invention also includes a "universal peroxisomal targeting sequence" ("UPTS") which can be appended (preferably fused or conjugated) to any protein or other molecule in order to target that protein or other molecule to peroxisomes. Preferred UPTS's have between 3 and about 20 amino acids, more preferably between 3 and about 16 residues, most preferably between about 8 and about 12 residues. For convenience, the residues are numbered from the C terminus using ascending negative integers as follows:

$NH_2$— ... $Xaa_{-n}$ ... $Xaa_{-4}Xaa_{-3}Xaa_{-2}Xaa_{-1}$—COO—.

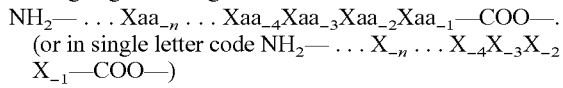

Thus, in a 12 residue UPTS, $Xaa_{-n}$ would be $Xaa_{-12}$ and n would equal 12.

Amino acids in any of the sequences of the invention may be naturally occurring amino acids, or non naturally-occurring amino acids or amino acid derivatives.

Accordingly, one embodiment of the invention is a modified catalase polypeptide having a carboxy-terminal peroxisome targeting signal (PTS) that has been modified from a native sequence of Lys-Ala-Asn-Leu (SEQ ID NO: 1) by replacement with a PTS comprising the sequence $Xaa_{-3}$, $Xaa_{-2}$, $Xaa_{-1}$ wherein, independently, (a) $Xaa_{-3}$ is Ser, Ala or Cys; (b) $Xaa_{-2}$ is Lys, Arg or His; and (c) $Xaa_{-1}$ is Leu or Met.

In a further embodiment of the invention, a modified catalase polypeptide as above further comprises, to the amino-terminal side of $Xaa_{-3}$. n additional amino acid residues wherein n is an integer between 1 and about 17, the additional residues being numbered sequentially from $Xaa_{-4}$ for the first additional residue to $Xaa_{-20}$ for the seventeenth additional residue. The additional amino acids may be naturally occurring ones, or modified variants thereof. Preferably, n is between about 5 and about 17 (e.g., between about 7 and about 13; or between about 9 and about 11; or 9). In another embodiment, n is at least 1, 2 or 3, and residues at any one of any one of $Xaa_{-6}$ to $Xaa_{-4}$ are hydrophobic amino acids (e.g., residues $Xaa_{-6}$ to $Xaa_{-4}$ are, independently, Leu (L), Val (V), Ile (I), Ala (A) or Gly (G)). In another embodiment, n is at least 1, and residue $Xaa_{-4}$ is a positively charged amino acid (e.g., residue $Xaa_{-4}$ is Lys (K), Arg (R) or His (H), preferably Lys (K)). Preferably, in any of the modified catalases of the invention, $Xaa_{-3}$ is Ser (S), $Xaa_{-2}$ is Lys (K), and $Xaa_{-1}$ is Leu (L). In one embodiment, the replacement PTS does not comprise the sequence Ser-Leu-Leu or the sequence Lys-Ala-Asn-Leu.

In another embodiment, catalase is modified by conjugation of a peptidomimetic of SKL that serves as a strong peroxisomal targeting signal to enhance import into peroxisomes. A preferred peptidomimetic compound mimics the biological effects of SKL or of a biologically active variant thereof. A peptidomimetic agent may be an unnatural peptide or a non-peptide agent that recreates the stereospatial properties of the binding elements of SKL such that it has the receptor-binding activity or biological activity of SKL (when it is at the C-terminus of catalase or in the form of a UPTS bonded to another protein). The preferred receptor to which the mimetic binds is Pex5p. Thus the mimetic would also be considered to be a "substrate" for Pex5p. Similarly to a biologically active SKL peptide, a peptidomimetic will have a binding face (which interacts with any ligand or receptor to which SKL binds). Also included are compounds that retain partial peptide characteristics. For example, any proteolytically unstable bond within a peptide of the invention could be selectively replaced by a non-peptidic element such as an isostere (N-methylation; D-amino acid) or a reduced peptide bond while the rest of the molecule retains its peptidic nature. Peptidomimetic compounds, either agonists, substrates or inhibitors, have been described for a number of bioactive peptides such as opioid peptides, VIP, thrombin, HIV protease, etc. Methods for designing and preparing peptidomimetic compounds are known in the art (Hruby, V. J., *Biopolymers* 33:1073-1082 (1993); Wiley, R. A. et al., *Med. Res. Rev.* 13:327-384 (1993); Moore et al., *Adv. in Pharmacol* 33:91-141 (1995); Giannis et al., *Adv. in Drug Res.* 29:1-78 (1997), which references are incorporated by reference in their entirety). These methods are used to make peptidomimetics that possess Pex5p binding specificity and biological activity of SKL. Knowledge of peptide chemistry and general organic chemistry available to those skilled in the art are sufficient, in view of the present disclosure, for designing and synthesizing such compounds. For example, such peptidomimetics may be identified by inspection of the crystallographically-derived 3D structure of a peptide of the invention either in free form, fused to another polypeptide, or bound in complex with a ligand/receptor such as Pex5p. Alternatively or additionally, the structure of a peptide can be obtained by the techniques of nuclear magnetic resonance spectroscopy. The better knowledge of the stereochemistry of the interaction of the peptide with its ligand or receptor will permit the rational design of such peptidomimetic agents.

In addition to the C-terminal PTS1-type molecules discussed above, a second, conserved, peroxisomal targeting sequence—a PTS2-type sequence—is naturally found in some peroxisomally located protein molecules (but not in catalase), at or near their N-terminus. The receptor for PTS2 is Pex7P. For a review of PTS2 sequences and functions, see Purdue et al., 2001. By "near" the N-terminus is meant within about 40 amino acids of the N-terminus. A consensus sequence for this 9 amino acid targeting moiety is: (Arg/Lys)-(Leu/Ile/Val)-(X$_5$)-(His/Gln)-(Ala/Leu/Phe). In a preferred embodiment, this targeting moiety has the amino acid sequence: RLQVVLGHL (SEQ ID NO: 11). Active variants of this sequence, in which, e.g., one or more conservative amino acid substitutions occur, are also included in the invention, provided that they retain peroxisomal targeting activity. One of skill in the art can readily test a putative sequence to determine if it retains the desired activity. Accordingly, a modified catalase polypeptide of the invention may comprise, in addition to, or instead of, a PTS1-type sequence at its C-terminus, a peptide having the consensus PTS2-type sequence described above, preferably having the sequence of SEQ ID NO: 11. The PTS2 sequence is preferably engineered to be at or near the N-terminus of the catalase polypeptide.

PTS1 and PTS2 sequences have been described for a variety of animal species, and can be "mixed and matched" in modified catalase proteins of the invention. Of course, when a PTS from one animal species is introduced into another species, it is preferable that cross-species antigenic effects do not occur.

A modified catalase molecule used in the compositions and methods of the invention can be derived from the catalase of any animal source, preferably mammalian, most preferably human. The modified catalase can be derived from (and reintroduced into), among others, an agricultural animal (e.g., a chicken, cow, sheep, goat or horse), a pet animal, or a human (e.g., a patient being treated for one or another disease or condition). When a catalase molecule from one animal species is introduced into another species, it is preferable that cross-species antigenic effects do not occur.

The sequence of a human catalase protein is (SEQ ID NO: 2)

```
  1 MADSRDPASD QMQHWKEQRA AQKADVLTTG AGNPVGDKLN
    VITVGPRGPL LVQDVVFTDE

61 MAHFDRERIP ERVVHAKGAG AFGYFEVTHD ITKYSKAKVF
    EHIGKKTPIA VRFSTVAGES

121 GSADTVRDPR GFAVKFYTED GNWDLVGNNT PIFFIRDPIL
    FPSFIHSQKR NPQTHLKDPD

181 MVWDFWSLRP ESLHQVSFLF SDRGIPDGHR HMNGYGSHTF
    KLVNANGEAV YCKFHYKTDQ

241 GIKNLSVEDA ARLSQEDPDY GIRDLFNAIA TGKYPSWTFY
    IQVMTFNQAE TFPFNPFDLT

301 KVWPHKDYPL IPVGKLVLNR NPVNYFAEVE QIAFDPSNMP
    PGIEASPDKM LQGRLFAYPD

361 THRHRLGPNY LHIPVNCPYR ARVANYQRDG PMCMQDNQGG
    APNYYPNSPG APEQQPSALE

421 HSIQYSGEVR RFNTANDDNV TQVRAFYVNV LNEEQRKRLC
    ENIAGHLKDA QIFIQKKAVK

481 NFTEVHPDYG SHIQALLDKY NAEKPKNAIH TFVQSGSHLA
    AREKANL
```

Also intended are modified catalase allelic variants of the above sequence, a number of which have been identified. The present invention includes catalases with the sequence of any of these variants, as well as allelic variants of catalases of non-human mammals. Modified forms of artificially created catalase variants and fragments of the types described elsewhere herein are also within the scope of the invention.

The sequence of a nucleic acid encoding the above noted human catalase protein, including a stop codon, is: (SEQ ID NO: 3)

```
atg gct gac agc cgg gat ccc gcc agc gac cag      48
atg cag cac tgg aag gag cag cgg gcc gcg cag aaa gct gat gtc ctg      96
acc act gga gct ggt aac cca gta gga gac aaa ctt aat gtt att aca     144
gta ggg ccc cgt ggg ccc ctt ctt gtt cag gat gtg gtt ttc act gat     192
gaa atg gct cat ttt gac cga gag aga att cct gag aga gtt gtg cat     240
gct aaa gga gca ggg gcc ttt ggc tac ttt gag gtc aca cat gac att     288
acc aaa tac tcc aag gca aag gta ttt gag cat att gga aag aag act     336
ccc atc gca gtt cgg ttc tcc act gtt gct gga gaa tcg ggt tca gct     384
gac aca gtt cgg gac cct cgt ggg ttt gca gtg aaa ttt tac aca gaa     432
gat ggt aac tgg gat ctc gtt gga aat aac acc ccc att ttc ttc atc     480
agg gat ccc ata ttg ttt cca tct ttt atc cac agc caa aag aga aat     528
cct cag aca cat ctg aag gat ccg gac atg gtc tgg gac ttc tgg agc     576
cta cgt cct gag tct ctg cat cag gtt tct ttc ttg ttc agt gat cgg     etc.
ggg att cca gat gga cat cgc cac atg aat gga tat gga tca cat act
ttc aag ctg gtt aat gca aat ggg gag gca gtt tat tgc aaa ttc cat
tat aag act gac cag ggc atc aaa aac ctt tct gtt gaa gat gcg gcg
aga ctt tcc cag gaa gat cct gac tat ggc atc cgg gat ctt ttt aac
gcc att gcc aca gga aag tac ccc tcc tgg act ttt tac atc cag gtc
atg aca ttt aat cag gca gaa act ttt cca ttt aat cca ttc gat ctc
acc aag gtt tgg cct cac aag gac tac cct ctc atc cca gtt ggt aaa
ctg gtc tta aac cgg aat cca gtt aat tac ttt gct gag gtt gaa cag
ata gcc ttc gac cca agc aac atg cca cct ggc att gag gcc agt cct
gac aaa atg ctt cag ggc cgc ctt ttt gcc tat cct gac act cac cgc
cat cgc ctg gga ccc aat tat ctt cat ata cct gtg aac tgt ccc tac
cgt gct cga gtg gcc aac tac cag cgt gat ggc ccg atg tgc atg cag
gac aat cag ggt ggt gct cca aat tac tac ccc aac agc ttt ggt gct
```

-continued

```
ccg gaa caa cag cct tct gcc ctg gag cac agc atc caa tat tct gga
gaa gtg cgg aga ttc aac act gcc aat gat gat aac gtt act cag gtg
cgg gca ttc tat gtg aac gtg ctg aat gag gaa cag agg aaa cgt ctg
tgt gag aac att gcc ggc cac ctg aag gat gca caa att ttc atc cag
aag aaa gcg gtc aag aac ttc act gag gtc cac cct gac tac ggg agc
cac atc cag gct ctt ctg gac aag tac aat gct gag aag cct aag aat
gcg att cac acc ttt gtg cag tcc gga tct cac ttg gcg gca agg gag
aag gca aat ctg tga
```

One embodiment of the invention comprises a method of introducing catalase into animal cells, such as human cells. In a clinical setting, this may be performed prophylactically, to slow down aging-related or other pathological processes before the various deficiencies associated with aging or certain diseases have manifested themselves. Compositions useful for this method comprise a catalase molecule that has attached thereto one or more PTSs (e.g., a UPTS) or mimetic of a PTS and, optionally, a further component which serves as a polypeptide or peptide delivery (as distinct from a "targeting") system. As used herein, "delivery' refers to bringing a molecule into a cell, whereas "targeting" refers to bringing a molecule into a peroxisome. Delivery molecules contemplated herein include polypeptides or peptides used by others to effect cellular entry. See for example, Morris et al., supra, incorporated by reference in its entirety. A preferred strategy is as follows: a newly engineered catalase molecule, e.g., catalase-SKL, is incubated with a specially designed peptide which "coats" the catalase and facilitates its entry into human cells. This delivery system does not require the delivery peptide to be fused to catalase, nor does catalase have to be denatured prior to the "transduction" process. A disadvantage of many earlier delivery systems is that they required denaturation of the "payload" protein prior to delivery and subsequent renaturation within the cell. This aspect of the invention is based on well-tested approaches for promoting protein translocation into cells. This method takes advantage of the fact that fully folded proteins, having been transduced across the plasma membrane, are capable of being imported into the peroxisome in this state.

One type of "delivery" peptide/polypeptide which promotes cell entry and translocation includes the HIV-TAT protein (Frankel, A D et al., Cell 55:1189-1193 (1998), and the third α helix from the Antennapoedia homeodomain (Derossi et al., *J. Biol. Chem.* 269:10444-10450 (1994); Lindgren, M et al., *Trends in Pharmacol. Sci.* 21:99-103 (2000). The latter peptide, also known as "penetratin" is a 16-amino acid peptide having the wild-type sequence RQIKIWFQNRRMKWKK (SEQ ID NO: 4) or two of its analogues/variants designated W48F (RQIKIFFQNRRMKWKK, SEQ ID NO: 5) and W56F (RQIKIWFQNRRMKFKK, SEQ ID NO: 6) (Christiaens B et al., *Eur J Biochem* 2002, 269:2918-2926). Another variant with both of the above mutations is also included (RQIKIFFQNRRMKFKK, SEQ ID NO: 7).

Another protein (family) includes VP22, a herpes simplex virus (HSV-1) protein that has the remarkable property of intercellular transport and is capable of distributing protein to many surrounding cells (Elliott, G et al., 1997, *Cell* 88.223-33; O'Hare & Elliott, U.S. Pat. No. 6,017,735). For example, VP22 has been linked to p53 (Phelan, A. et al., 1998, *Nat Biotechnol* 16:440-3) or thymidine kinase (Dilber, M S et al., 1999, *Gene Ther* 6.12-21) facilitating the spread of linked proteins to surrounding cells in vitro. VP22 has "homologues" in other herpes viruses, such as the avian Marek's Disease Virus (MDV). Marek's disease virus type 1 UL49 shares homology with HSV-1 VP22 (Koptidesova et al., 1995, *Arch Virol.* 140, 355-362) and has been shown to be capable of intercellular transport after exogenous application (Dorange et al., 2000, *J Gen Virol.* 81 *Pt* 9:2219-2230). All these proteins have the property of intercellular spread that provide an approach for enhancing cellular uptake of the modified catalase of this invention.

Also included are "functional derivatives" of the above intercellular spreading or "delivery" proteins such as HIV-TAT or VP22 which include homologous amino acid substitution variants, "fragments" or chemical derivatives, which terms are defined below. A functional derivative retains measurable translocation or intercellular spreading (VP22-like) activity that promotes the successful entry of the desired protein, preferably a modified catalase, into cells so that it may then be effectively imported into peroxisomes. This process permits the protein's utility, e.g., therapeutic, in accordance with the present invention. "Functional derivatives" encompass "variants" and "fragments" regardless of whether the terms are used in the conjunctive or the alternative herein.

Because the above transport proteins are said to work best when conjugated or otherwise bound the protein they are transporting, such as, a targeted catalase, there are a number of disadvantages when using them. A more effective delivery polypeptide that can be admixed with the targeted catalase and does not need to be chemically bonded for its action is described in Morris et al., supra, as Pep-1, which has the following amphipathic amino acid sequence—KETWWETWWTEWSQPKKKRKV (SEQ ID NO: 8). Pep-1 consists of three domains:

(1) a hydrophobic Trp-rich motif containing five Trp residues (KETWWETWWTEW, SEQ ID NO: 9), the N-terminal 12 residues of SEQ ID NO: 8 above). This motif is desirable, or required, for efficient targeting to the cell membrane and for entering into hydrophobic interactions with proteins;

(2) a hydrophilic Lys-rich domain (KKKRKV, SEQ ID NO: 10), the 6 C-terminal residues of a sequence derived from the nuclear localization sequence of SV-40 virus large T antigen, which improves intracellular delivery and solubility of the peptide vector; and (3) a spacer domain (SQP) which are internal residues of SEQ ID NO: 8 and separate the two active domains, and include a proline that improves flexibility and integrity of both the hydrophobic and hydrophilic domains.

Accordingly, another embodiment of the invention is a deliverable, peroxisomally-targeted polypeptide comprising a modified catalase of the invention and a delivery or translocation-molecule or moiety bound thereto or associated therewith. The delivery molecule may be a peptide or polypeptide, e.g., (a) HIV-TAT protein or a translocationally active derivative thereof, (b) penetratin having the sequence RQIKIWFQNRRMKWKK (SEQ ID NO: 4), (c) a penetratin variant W48F having the sequence RQIKIFFQNRRMKWKK (SEQ ID NO: 5)

(d) a penetratin variant W56F having the sequence RQIKIVFQNRRMKFKK, SEQ ID NO: 6)

(e) a penetratin variant having the sequence RQIKIWFQNRRMKFKK, SEQ ID NO: 7)

(f) herpes simplex virus protein VP22 or a translocationally-active homologue thereof from a different herpes virus; or (g) Pep-1, having the sequence KETWWETWWTEWSQPKKKRKV (SEQ ID NO: 9).

When a delivery protein, such as the peptides discussed above, and a PTS2 type sequence are present in a modified catalase polypeptide, the order of the sequences, proceeding from the N-terminus, is preferably: the "delivery sequence"; the PTS2 type sequence; the N-terminus of catalase.

As is discussed in more detail below, a deliverable, peroxisomally targeted polypeptide may be associated with a liposome. Accordingly, another aspect of the invention is a deliverable polypeptide of the invention (such as a modified catalase polypeptide), wherein the delivery moiety associated with the modified catalase is a liposome. In one embodiment, the liposome comprises effective concentrations of external membrane phosphatidylserine for uptake by phagocytic cells or other phosphatidylserine-recognizing cells.

A modified catalase polypeptide of the invention can be of any suitable length, provided that it retains the ability to reduce the level of $H_2O_2$ and, indirectly, the level of other ROS, in a peroxisome and, consequently, in a cell. The location and properties of the catalytic sites of catalase proteins from a variety of sources are well-known to those of skill in the art. Therefore, for example, a modified catalase protein of the invention can be as small as a peptide that consists essentially of one or more catalytic sites of the protein (plus, of course, a C-terminal PTS1-type sequence of the invention and/or an N-terminal PTS2-type sequence and, optionally, a delivery sequence as discussed above). Larger fragments are also encompassed, including fragments ranging in size from molecules containing, in addition to a catalytic site, about 1-20 additional amino acids on either or both sides of the catalytic site, to molecules that are only one amino acid shorter than the full-length catalase protein (plus the C-terminal PTS sequences, N-terminal PTS sequences or delivery sequences as discussed above). Methods to generate suitable fragments, and to establish that they retain enzymatic activity, are routine and conventional. The terms protein, polypeptide and peptide are sometimes used interchangeably herein. The length of a "polypeptide" is not intended to be limited to any particular size; thus "polypeptides" and "peptides" overlap.

One embodiment of the invention is a polynucleotide (e.g., an isolated polynucleotide) encoding a modified catalase polypeptide of the invention, wherein the coding sequence is operably linked to an expression control sequence. (The terms polynucleotide and nucleic acid are used interchangeably herein.) The polynucleotide may encode any modified catalase polypeptide of the invention, which comprises a PTS1 and/or PTS2 sequence as discussed above. Optionally, the polynucleotide may further encode a delivery peptide as discussed above, fused in frame at or near the N-terminus of the modified catalase. The sequence of a polynucleotide that encodes a polypeptide of the invention may differ from a naturally occurring sequence. For example, the polynucleotide may reflect the degeneracy of the genetic code; and/or it may encode a variant polypeptide of the types discussed elsewhere herein. Polynucleotides of the invention are useful, e.g., for expressing the modified catalase polypeptide recombinantly in a host cell, as a method for preparing the modified catalase for further use, in vitro or in vivo.

As used herein, the term "expression control sequence" means a polynucleotide sequence that regulates expression of a polypeptide coded for by a polynucleotide to which it is functionally ("operably") linked. Expression can be regulated at the level of the mRNA or polypeptide. Thus, the term expression control sequence includes mRNA-related elements and protein-related elements. Such elements include promoters, domains within promoters, upstream elements, enhancers, elements that confer tissue or cell specificity, response elements, ribosome binding sequences, transcriptional terminators, etc. An expression control sequence is operably linked to a nucleotide sequence (e.g., a coding sequence) when the expression control sequence is positioned in such a manner to effect or achieve expression of the coding sequence. For example, when a promoter is operably linked 5' to a coding sequence, expression of the coding sequence is driven by the promoter.

Suitable expression control sequences can be selected for host compatibility and desired purpose. These include, e.g., enhancers such as from SV40, CMV, RSV, inducible or constitutive promoters, and cell-type or tissue-type specific elements or sequences that allow selective or specific cell expression. Promoters that can be used to drive expression, include, e.g., an endogenous promoter, MMTV, SV40, CMV, c-fos, β-globin etc. for mammalian host cells; trp, lac, tac, or T7 promoters for bacterial hosts; or alpha factor, alcohol oxidase, or PGH promoters for yeast. See, e.g., Melton et al. (1984) *Polynucleotide Res.* 12(18), 7035-7056; Dunn et al. (1984) *J. Mol. Bio.* 166, 477-435; U.S. Pat. No. 5,891,636; Studier et al. (1987) Gene Expression Technology, in *Methods in Enzymology*, 85, 60-89. A natural expression control sequence of a gene may be used to express the peptide recombinantly, e.g., an expression control sequence from a catalase protein can be used to drive the expression of a recombinant modified catalase polypeptide of the invention.

Methods of making recombinant constructs, in which a sequence encoding a protein of interest, such as a modified catalase polypeptide, is operatively linked to an expression control sequence, are conventional. In general, a coding sequence of interest is operably linked to an expression control sequence in an expression vector. A construct (a recombinant construct) generated in this manner can express the protein when introduced into a cell. Methods of making recombinant constructs, as well as many of the other molecular biological methods used in conjunction with the present invention, are discussed, e.g., in Sambrook, et al. (1989), *Molecular Cloning, a Laboratory Manual*, Cold Harbor Laboratory Press, Cold Spring Harbor, N.Y.; Ausubel et al. (1995). *Current Protocols in Molecular Biology*, N.Y., John Wiley & Sons; Davis et al. (1986), *Basic Methods in Molecular Biology*, Elseveir Sciences Publishing, Inc., New York; Hames et al. (1985), *Nucleic Acid Hybridization*, IL Press; Dracopoli et al. *Current Protocols in Human Genetics*, John Wiley & Sons, Inc.; and Coligan et al. *Current Protocols in Protein Science*, John Wiley & Sons, Inc.

A sequence of interest placed under the control of a suitable expression control sequence is generally cloned into a suitable vector, to form a "construct." Large numbers of suitable vectors are known to those of skill in the art, and many are commercially available. The following vectors are provided by way of example; Bacterial: pQE70, pQE60, pQE-9 (Qiagen), pBS, pD10, phagescript, psiX174, pBluescript SK, pBSKS, pNH8A, pNH16a, pNH18A, pNH46A (Stratagene); pTRC99a, pKK223-3, pKK233-3, pDR540, pRIT5 (Pharmacia); Eukaryotic: pWLNEO, pSV2CAT, pOG44, pXT1, pSG (Stratagene) pSVK3, pBPV, pMSG, pSVL (Pharmacia). However, any other plasmid or vector may be used as long as it is replicable and viable in the host. Suitable host cells will be evident to the skilled worker and include, e.g., prokaryotes, yeast, insect and animal, including mammalian, cells. Large amounts of the construct, and/or of the polypeptide encoded thereby, can be prepared by expressing the construct in a suitable host cell.

Methods to introduce polynucleotides of the invention into cells (to "contact" the cells) in vitro will be evident to the skilled worker. These include, e.g., transfection (e.g., mediated by DEAE-Dextran or calcium phosphate precipitation), infection via a viral vector (e.g., retrovirus, adenovirus, adeno-associated virus, lentivirus, pseudotyped retrovirus or poxvirus vectors), injection, such as microinjection, electroporation, sonoporation, a gene gun, liposome delivery (e.g., Lipofectin®, Lipofectamine® (GIBCO-BRL, Inc., Gaithersburg, Md.), Superfect® (Qiagen, Inc. Hilden, Germany) and Transfectam® (Promega Biotec, Inc., Madison, Wis.), or other liposomes developed according to procedures standard in the art), or receptor-mediated uptake and other endocytosis mechanisms. As a skilled worker will recognize, some of the preceding methods may also be used to "contact" cells in vivo. Other methods for contacting cells in vivo with polypeptides of the invention (e.g., methods for administering them to a subject in need thereof) are discussed below.

Cells comprising a polynucleotide of the invention may be incubated under conditions effective for the expression of the recombinant polypeptide encoded by the polynucleotide. Effective conditions will be evident to the skilled worker. These include, e.g., temperature, concentration of $O_2$ or $CO_2$, suitable culture vessels and media, or the like, all of which are routinely optimizable. Methods of harvesting and isolating (e.g., purifying) the polypeptide are conventional and well known to those of skill in the art.

Another method for generating a modified catalase polypeptide of the invention, or a nucleic acid encoding it, involves producing a polypeptide or polynucleotide by chemical synthesis, using conventional procedures. Portions of a polypeptide or polynucleotide (such as, e.g., a portion of catalase, such as an active site; a PTS; or a delivery peptide, or a polynucleotide encoding such peptides) can be produced synthetically, then joined to other polypeptides or polynucleotides that have been produced synthetically, or joined to one or more molecules that have been produced recombinantly or that have been isolated from a natural source. Procedures for joining such molecules are conventional.

In other embodiments, the present invention is directed to the use of a targeted catalase of the invention in various physiological, pharmaceutical or therapeutic compositions, e.g., to treat age-related and/or free radical-related human cellular pathologies. Conditions (including disease conditions or disorders) that can be prevented or treated by methods of the invention include conditions associated with peroxisomal abnormalities or deficiencies, particularly those resulting in abnormally low availability or levels of catalase and consequent rises in levels of intracellular $H_2O_2$ and generation of ROS. Methods for preventing or treating such conditions comprise reducing the levels of $H_2O_2$ and other ROS in a peroxisome and, consequently, in a cell, and subsequently in the surrounding tissue.

In general, the invention relates to methods for treating a subject (e.g., a mammal, such as a human) suffering from a condition (e.g., a disease) that is associated with an inadequate level of peroxisomal catalase, comprising administering to the subject an effective amount of a modified catalase of the invention, preferably administering a deliverable, modified catalase of the invention. Among the types of conditions that can be prevented or treated by methods of the invention are, e.g., (1) diseases of the skin, preferably to protect the skin against age-related changes and cancer radiation-induced damage; (2) ischemia, particularly to protect against reperfusion injury; (3) lowering of serum lipids in conjunction with agents given to treat hyperlipidemias, in part because certain hypolipidemic agents promote liver cancer; (4) neurodegenerative diseases; and (5) aging.

The catalase enzyme may be used in methods of the invention in a form in which an iron atom is present in the catalystic site. Alternately, the apoenzyme form of the enzyme, lacking an iron atom, may be used.

One preferred use of the UPTS and peptide delivery system, and, particularly, the catalase targeting and delivery system of the present invention is for administration to skin in a topical carrier, for example, a cream, to prevent and/or treat an age-related skin alteration. Correctly targetable catalase, introduced into human basal skin cells, will enter peroxisomes and contribute to the prevention of age-dependent changes and protection from the sunlight-induced changes to the skin. Since a catalase solution at certain concentrations has a green color due to the iron atoms associated with the enzyme's active site, the substance may appear unappealing to a potential user. This may be managed by either using the catalase apoenzyme lacking the metal atoms or by inclusion of dye materials in the vehicle formulation to alter the color of, for example, the solution or cream.

As noted above, the present targeted catalase technology can be used to extend the life-span of cells, including human cells. Cells normally senesce at population doublings of 50 or 60. By introducing engineered catalase into the cells and into their peroxisomes, the population doubling number is predicted to increase. The present compositions can be used to prolong life span at the cellular and the organismic levels. For example, the population doubling number in stem cells can be increased, as can the longevity of certain artificial organs. Ultimately, the compositions are applicable to increasing the life span of, e.g., agricultural animals, pets, cloned animals or humans.

The present technology is applicable to the field of tissue engineering—specifically in an attempt to keep stem and progenitor cells from aging. These cells are very difficult (and expensive) to prepare; any mechanism by which they could be rendered functional for longer periods of time is of great interest. Thus, in one embodiment, the compositions of the present invention are delivered to cultured stem cells of any class or type, including totipotent stem cells, pluripotent hemopoietic stem cells, committed stem cells of any lineage, including neural, cardiac, liver, bone, muscle, etc. stem cells, and stem cells present in any tissue, organ body cavity or body fluid. By entry into cells and targeting to peroxisomes, the compositions disclosed above, such as catalase-SKL, prolong the life span of stem cells while these are maintained in a "youthful" state, and/or inhibit senescence in vitro arising from multiple rounds of division. In one embodiment, such treatment of stem or progenitor cells increases the longevity of an artificial organ.

It is noted that this targeted catalase technology seeks to increase life-span, not by removing natural barriers that prevent damaged cells from dividing, but instead by preventing the free radicals from accumulating and induced damage from ever occurring.

One manifestation of ischemia of the heart or brain is ROS-induced damage, which results in tremendous damage to the tissue of these organs. Much of the pathology results from ROS, which accumulate, particularly during the period of reperfusion. This is a serious problem in patients who are receiving medical treatment yet suffer morbidity and mortality due to the reintroduction of oxygen to affected tissues. According to this invention, the peroxisomal targeting technology, preferably coupled with improved delivery into cells of targeted catalase or other proteins, is applicable in preventing reperfusion injury and for other uses in treatment of ischemia. The timely presence of high levels of properly targeted catalase in tissues experiencing free radical assault would benefit the recovery of the patient.

The preferred animal subject of the present invention is a mammal. The invention is particularly useful in the treatment of human subjects. By the term "treating" is intended the administering to subjects of a pharmaceutical composition comprising a modified catalase of the present invention. The therapeutic composition, such as a combination of targeted catalase (e.g., having an UPTS such as SKL or AKL at its C-terminus) mixed with Pep-1, is administered to a mammalian subject, preferably a human, in a pharmaceutically acceptable carrier in a biologically effective or a therapeutically effective amount. The composition may be given alone or in combination with another agent. For example, it may be administered in conjunction with a polypeptide or peptide having superoxide dismutase (SOD) activity, or with a small molecule that stimulates SOD activity. A therapeutically effective amount is a dosage that, when given for an effective period of time, achieves a measurable clinical effect.

A therapeutically active amount of the present composition may vary according to factors such as the disease state, age, sex, and weight of the individual, and the ability of the composition to elicit a desired response in the individual. Dosage regimes may be adjusted to provide the optimum therapeutic response. For example, several divided doses may be administered daily or the dose may be proportionally reduced as indicated by the exigencies of the therapeutic situation.

An effective amount of the targeted catalase is generally between about 1 nanogram and about 50 milligram per kilogram of body weight of the recipient, more preferably between about 1 µg and 10 mg/kg. Dosage forms suitable for internal administration preferably contain (for the latter dose range) from about 0.01 µg to 100 µg of active ingredient per unit. The active ingredient may vary from 0.5 to 95% by weight based on the total weight of the composition. Those skilled in the art of therapy of conditions associated with peroxisomal deficiencies, including that due to normal aging, will be able to adjust these doses without undue experimentation.

The active compound may be administered in a convenient manner, e.g., injection by a convenient and effective route. Preferred routes include subcutaneous, intradermal, intravenous, intraperitoneal, and intramuscular routes. Other possible routes include topical, oral, intrathecal, inhalation, transdermal or rectal administration.

One preferred embodiment of this invention is the present targeted catalase compositions in a topical pharmaceutical (and/or cosmetic) formulation for treating human skin to prevent or improve aging-related changes.

Other possible cosmetically acceptable carriers can include liquid petrolatum, isopropyl palmitate, polyethylene glycol, ethanol (95%), polyoxyethylene monolauriate (5%) in water, sodium lauryl sulfate (5%) in water. Other materials such as anti-oxidants, humectants, viscosity stabilizers (for aqueous injection suspensions), and similar agents may be added as desired. In addition, fragrances may be added to the compositions to improve their scent or colored agents to enhance their appearance.

Such formulations may include any of a number of exemplary oils including mineral oils (liquid petrolatum), plant oils (liquid fraction of karite butter, sunflower oil, sesame oil), animal oils (perhydrosqualen(e), synthetic oils (purcellin oil), silicone oils (cyclomethicone) and fluoro-oils (perfluoropolyethers). Fatty alcohols, fatty acids (stearic acid) or synthetic fatty acid esters (ethyl oleate or triglycerides) and waxes (paraffin wax, carnauba wax and beeswax) may also be used as fats.

As used herein, a "cosmetically acceptable topical carrier" or a "cosmetically acceptable vehicle" refers to a carrier, a diluent, or a dispersant capable of delivering a targeted catalase in combination with a cell delivery peptide/polypeptide to the skin (or to an appropriate layer thereof) without undue toxicity, irritation, allergenicity, or the like. In addition, to be cosmetically acceptable, the topical carrier preferably possesses favorable cosmetic properties such as overall feel, ability to be rubbed in, lack of excessive greasiness, etc. Most preferred topical carriers are organic materials in which the active agent can be dispersed or dissolved Sagarin, E et al., (1972) *Cosmetics, Science and Technology*, 2d ed., 1:48-65), incorporated herein by reference, contains numerous examples of suitable cosmetically acceptable topical carriers. Examples include various emollients, emulsifiers, humectants, thickeners and powders, and solvents (including water) as described below.

Examples of cosmetically acceptable organic solvents are propylene glycol, polyethylene glycol (200-600), polypropylene glycol (425-2025), glycerol, sorbitol esters, 1,2,6-hexanetriol, ethanol, isopropanol, butanediol, and mixtures thereof.

The cosmetically acceptable vehicle will usually form from 5% to 99.9%, preferably from 25% to 80% by weight of the active composition, and can, in the absence of other cosmetic adjuncts, form the balance of the composition.

The compositions may be in the form of aqueous, aqueous/alcoholic or oily solutions; dispersions of the lotion or serum type; anhydrous or lipophilic gels; emulsions of liquid or semi-liquid consistency, which are obtained by dispersion of a fatty phase in an aqueous phase or vise versa; or suspensions or emulsions of smooth, semi-solid or solid consistency of the cream or gel type. These compositions are formulated according to the usual techniques well known in the art.

When a composition of the invention is formulated as an emulsion, the proportion of the fatty phase may range from 5% to 80% by weight, preferably from 5% to 50%, relative to the total weight of the composition. Oils, emulsifiers and co-emulsifiers incorporated in the composition in emulsion form are selected from among those used conventionally in the cosmetic or dermatology field. An emulsifier and coemulsifier may be present in the composition at a proportion ranging from 0.3% to 30% by weight, preferably from 0.5% to 20%, relative to the total weight of the composition.

When the compositions of the invention are formulated as an oily solution or gel, the fatty phase may constitute more than 90% of the total weight of the composition.

The compositions of the invention may also contain additives and adjuvants which are conventional in the cosmetic, pharmaceutical or dermatological field, such as hydrophilic or lipophilic gelling agents, hydrophilic or lipophilic active agents, preservatives, antioxidants, solvents, fragrances, fillers, bactericides, odor absorbers and dyestuffs or colorants. The amounts of these various additives and adjuvants are those conventionally used in the art, and, for example, range from 0.01% to 10% of the total weight of the composition. Depending on their nature, these additives and adjuvants may be introduced into the fatty phase, or into the aqueous phase.

Hydrophilic gelling agents include carboxyvinyl polymers (carbomer), acrylic copolymers such as acrylate-alkylacrylate copolymers, polyacrylamides, polysaccharides, such as hydroxypropylcellulose, natural gums and clays, and, as lipophilic gelling agents, representative are the modified clays such as bentones, fatty acid metal salts such as aluminum stearates and hydrophobic silica, or ethylcellulose and polyethylene.

An oil or oily material may be present, together with an emollient to provide either a water-in-oil emulsion or an oil-in-water emulsion, depending largely on the average hydrophilic-lipophilic balance (HLB) of the emollient employed. Levels of such emollients may range from about 0.5% to about 50%, preferably between about 5% and 30% by weight of the total composition. Emollients may be classified as esters, fatty acids and alcohols, polyols and hydrocarbons.

Esters may be mono- or di-esters. Acceptable fatty diesters include dibutyl adipate, diethyl sebacate, diisopropyl dimerate, and dioctyl succinate. Acceptable branched chain fatty esters include 2-ethyl-hexyl myristate, isopropyl stearate and isostearyl palmitate. Acceptable tribasic acid esters include triisopropyl trilinoleate and trilauryl citrate. Acceptable straight chain fatty esters include lauryl palmitate, myristyl lactate, oleyl eurcate and stearyl oleate. Preferred esters include coco-caprylate/caprate (a blend of coco-caprylate and coco-caprate), propylene glycol myristyl ether acetate, di-isopropyl adipate and cetyl octanoate.

Suitable fatty alcohols and acids include those compounds having chains of 10 to 20 carbon atoms. Especially preferred are such compounds such as cetyl, myristyl, palmitic and stearyl alcohols and acids.

Among polyols which may serve as emollients are linear and branched chain alkyl polyhydroxyl compounds. For example, propylene glycol, sorbitol and glycerin are preferred. Also useful may be polymeric polyols such as polypropylene glycol and polyethylene glycol. Butylene and propylene glycol are also especially preferred as penetration enhancers.

Exemplary hydrocarbon has hydrocarbon chains anywhere from 12 to 30 carbon atoms. Specific examples include mineral oil, petroleum jelly, squalene and isoparaffins.

Another category of functional ingredients within the cosmetic compositions of the present invention are thickeners. A thickener will usually be present in amounts anywhere from 0.1 to 20% by weight, preferably from about 0.5% to 10% by weight of the composition. Exemplary thickeners are cross-linked polyacrylate materials available under the trademark Carbopol®. Gums may be employed such as xanthan, carrageenan, gelatin, karaya, pectin, and locust beans gum. Under certain circumstances the thickening function may be accomplished by a material also serving as a silicone or emollient. For instance, silicone gums in excess of 10 centistokes and esters such as glycerol stearate have dual functionality.

Powders may be incorporated into the cosmetic composition of the invention. These powders may include chalk, talc, kaolin, starch, smectite clays, chemically modified magnesium aluminum silicate, organically modified montmorillonite clay, hydrated aluminum silicate, fumed silica, aluminum starch octenyl succinate, and mixtures thereof.

The compositions may be in the form of a lyophilized particulate material, a sterile or aseptically produced solution. Vehicles, such as water (preferably buffered to a physiologically acceptable pH, as for example, in phosphate buffered saline) or other inert solid or liquid material such as normal saline or various buffers may be present. The particular vehicle should be selected to optimize the composition for topical or subcutaneous administration.

In general terms, a pharmaceutical/cosmetic composition is prepared by mixing, dissolving, binding or otherwise combining the targeted catalase composition with one or more water-insoluble or water-soluble aqueous or non-aqueous vehicles. If necessary, another suitable additive or adjuvant can be included. It is imperative that the vehicle, carrier or excipient, as well as the conditions for formulating the composition are such that do not adversely affect the biological or pharmaceutical activity of the proteins or peptides.

In the present method, the compositions can be given one time but generally is administered on multiple occasions, possibly on a regular basis for weeks, months or years. as is within the skill of the art to determine empirically. The treatments can be performed daily (or more than once per day) but are generally carried out every two to three days or as infrequently as once a week, as is beneficial, desired or necessary. Dosage and duration requirements between subjects may vary due to skin and body type. Typically between about 1.0 ng—about 1.0 g, preferably about 1.0 µg—about 100 mg, and most preferably between about 100 µg to about 10 mg, of the targeted catalase, preferably in combination with a cell-delivery polypeptide in an appropriate proportion, is included within the composition. In any event, it would be within routine skill in the art to determine empirically the frequency and/or dosage required to achieve the desired outcome(s).

The active agents are preferably incorporated into topically applied vehicles such as solutions, suspensions, emulsions, oils, creams, ointments, powders, liniments, salves, and the like, as a means for administering the active ingredient(s) directly to the desired area. The carrier for the active agent may be either in sprayable or non-sprayable form. Non-sprayable forms can be semi-solid or solid forms comprising a carrier indigenous to topical application and having a dynamic viscosity preferably greater than that of water. If desired, these may be sterilized or mixed with auxiliary agents, e.g., preservatives, stabilizers, wetting agents, buffers, or salts for influencing osmotic pressure and the like. Examples of preferred vehicles for non-sprayable topical preparations include ointment bases, e.g., polyethylene glycol-1000 (PEG-1000); conventional creams such as HEB cream; gels; as well as petroleum jelly and the like.

For the preferred topical application to human skin, it is preferred to administer an effective amount of a compound according to the present invention to the desired skin surface. This amount will generally range from about 0.001 mg to about 1 g per application, depending upon the area to be treated and the nature of the topical vehicle employed. A preferred topical preparation is an ointment wherein about 0.01 mg to about 50 mg of active ingredient is used per ml of ointment base, such as PEG-1000.

Depending on the route of administration, the active compound(s) may be coated in a material to protect the compound from the action of enzymes, acids and other natural conditions which may inactivate the compound. Thus it may be necessary to coat the composition with, or co-administer the composition with, a material to prevent its inactivation. For example, one can use enzyme inhibitors of nucleases or proteases (e.g., pancreatic trypsin inhibitor, diisopropylfluorophosphate and trasylol) or appropriate carriers such as liposomes (including water-in-oil-in-water emulsions as well as conventional liposomes) (Strejan et al., (1984) *J. Neuroimmunol* 7:27).

Modified catalase polypeptides or other polypeptides for peroxisomal targeting, including fusion proteins, conjugates, fragments, variants, etc. may be administered via implantable controlled release (or "sustained release") formulations and matrices. These formulations include but are not limited to poly-(D-, L- or DL-lactic acid/polyglycolide) polymer, ethylene-vinyl acetate (EVAc: Elvax 40W, Dupont) which is applicable to polypeptides in general—bioerodible polyanhydrides, polyimino carbonate, sodium alginate microspheres, hydrogels, D and poly DL (lactide/glycolide) copolymers, among others which are given in great detail in the following patents and publications which are hereby incorporated by reference (U.S. Pat. Nos. 4,891,225, 4,942,035, 4,877,606, 4,906,474, 4,806,621, 4,789,516, 4,925,677, EP 92918B1, EP No. EPO166596B1; Jeyanthi, R et al., *J. Controlled Release*, 13:91-98 (1990); Greig, N et al. *J. Controlled Release* 11:61-78 (1990); Kaitsu, I. et al., *J. Controlled Release* 6: 249-263 (1987); Yang, M. B. et al., *Cancer Res* 49:5103-5107 (1989); Eckenhoff, B et al., Biomaterials 2:89 (1981)).

Sickled erythrocytes may serve as carriers of modified catalase polypeptides. Sickled erythrocytes are known to be more adherent to microvascular endothelium than normal erythrocytes and to adhere to a greater extent under conditions of local hypoxia and acidosis. Hypoxemic conditions have no effect on adherence of normal erythrocytes but sickle erythrocyte adherence to endothelial cells is increased significantly. The polymerization of deoxygenated hemoglobin S results in a distortion of the shape of the red cell and marked decrease in its deformability. These rigid cells are responsible for the vaso-occlusive phenomena of sickle cell disease. This increased adherence to the microvascular endothelium occurs because of abnormally increased expression of $\alpha_4\beta_1$ integrin and CD36. As a region becomes more hypoxic, VCAM-1 and P-selectin expression on reactive endothelium is upregulated, trapping even more circulating sickled cells in the region.

In the present invention, when it is desired to deliver a modified catalase polypeptide, or a nucleic acid encoding the modified polypepeptide, to cells in the endothelium, particulary in microvasculature, sickled erythrocytes may be used as delivery vehicles. Use of sickle cell trait cells (from heterozygotes) are preferred since they are normal under physiologic conditions but sickle and become adhesive in acidotic and/or hypoxemic microvasculature. Use of such sickle cells for delivery of agents to tumors as been described. A sickled cell may be transfected or transduced with a gene of interest at a differentiation stage that precedes enucleation. Nucleated sickle reticulocytes are the preferred stage for introducing the genetic material although enucleated sickled cells will also work.

The sickled erythrocytes are administered parenterally by injection or infusion. First, however, the sickled erythorcytes are tested for ABO and Rh phenotypes to select compatible cells. Preferably, the cells are delivered intravenously or intraarterially in a blood vessel perfusing a specific site or organ of interest, e.g. carotid artery, portal vein, femoral artery, etc. over the same amount of time required for the infusion of a conventional blood transfusion and in a therapeutically effective amount of cells (i.e., that deliver a therapeutic amount of the composition). This may encompass a volume of 1-25 ml of packed cells administered i.v. over a one hour period. The treatments are generally given every three days although treatment schedules are flexible and may be extended or shortened depending upon a patient's response.

One embodiment of the invention is a pharmaceutical composition comprising any of the modified catalase polypeptides of the invention and a pharmaceutically acceptable excipient or carrier.

As used herein "pharmaceutically acceptable carrier" includes any and all solvents, dispersion media, coatings, antibacterial and antifungal agents, isotonic and absorption delaying agents, and the like. The use of such media and agents for pharmaceutically active substances is well known in the art. Except insofar as any conventional media or agent is incompatible with the active compound, use thereof in the therapeutic compositions is contemplated. Supplementary active compounds can also be incorporated into the compositions.

Preferred pharmaceutically acceptable diluents include saline and aqueous buffer solutions. Pharmaceutical compositions suitable for injection include sterile aqueous solutions (where water soluble) or dispersions and sterile powders for the extemporaneous preparation of sterile injectable solutions or dispersion. Isotonic agents, for example, sugars, polyalcohols such as mannitol, sorbitol, sodium chloride may be included in the pharmaceutical composition. In all cases, for internal uses, the composition should be sterile and should be fluid. It should be stable under the conditions of manufacture and storage and must include preservatives that prevent contamination with microorganisms such as bacteria and fungi. Dispersions can also be prepared in glycerol, liquid polyethylene glycols, and mixtures thereof and in oils. Under ordinary conditions of storage and use, these preparations may contain a preservative to prevent the growth of microorganisms.

The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants.

Prevention of the action of microorganisms can be achieved by various antibacterial and antifungal agents, for example, parabens, chlorobutanol, phenol, ascorbic acid, thimerosal, and the like.

Parenteral compositions are preferably formulated in dosage unit form for ease of administration and uniformity of dosage. Dosage unit form refers to physically discrete units suited as unitary dosages for a mammalian subject; each unit contains a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

For lung instillation, aerosolized solutions are used. In a sprayable aerosol preparations, the active protein may be in combination with a solid or liquid inert carrier material. This may also be packaged in a squeeze bottle or in admixture with a pressurized volatile, normally gaseous propellant. The aerosol preparations can contain solvents, buffers, surfactants, and antioxidants in addition to the protein of the invention.

Other pharmaceutically acceptable carriers for the compositions according to the present invention are liposomes, pharmaceutical compositions in which the active protein is contained either dispersed or variously present in corpuscles consisting of aqueous concentric layers adherent to lipidic layers. The active protein is preferably present in the aqueous layer and in the lipidic layer, inside or outside, or, in any event, in the non-homogeneous system generally known as a liposomic suspension. The hydrophobic layer, or lipidic layer, generally, but not exclusively, comprises phospholipids such as lecithin and sphingomyelin, steroids such as cholesterol, more or less ionic surface active substances such as diacetylphosphate, stearylamine or phosphatidic acid, and/or other materials of a hydrophobic nature.

In a preferred embodiment, liposomes that carry, for example, catalase-SKL, are designed so that their surface is rich in phosphatidylserine (PS). There has been a great deal of investigation into the aminophospholipid content of inner and outer membrane leaflests in cells, In normal, healthy young cells, PS is found in relatively high concentration on the cytoplasmic side of the cell membrane, whereas phosphatidylethanolamine (PE) is found in relatively high concentrations on the outer surface of the membrane. This PE/PS ratio (outside/inside) is inverted in aging cells, or in some types of cancer cells. Phagocytic clearance of aging or apoptotic cells is effected in part by recognition of the external PS by receptors on phagocytic cells such as macrophages, as well as other cell types involved in clearance. Thus the external PS tends to "mark a cell" for uptake. This may be seen not only in vitro but also when such liposomes are injected in vivo and taken up at particular sites such as liver sinusoids and brain. See, for example, Kagan V E et al., Am J Physiol Lung Cell Mol Physiol. 2003 July; 285(1):L1-17; Borisenko G G et al., Arch Biochem Biophys. 2003 May 1; 413(1):41-52; Balasubramanian K et al., Annu Rev Physiol. 2003; 65:701-34. Epub 2002 May 1; Manno S, et al. 7: Proc Natl Acad Sci USA. 2002 Feb. 19; 99(4):1943-8; Hoffmann P R et al. J Cell Biol. 2001 Nov. 12; 155(4):649-59; Schlegel R A et al., Cell Death Differ. 2001 June; 8(6):551-63; Schlegel R A et al., Ann N Y Acad Sci. 2000; 926:217-25; Fadok V A et al. J Biol Chem. 2001 Jan. 12; 276(2):1071-7; Witting A et al., J Neurochem. 2000 September; 75(3):1060-70; Kamps J A et al., Biochem Biophys Res Commun. 1999 Mar. 5; 256(1):57-62; Bevers E M et al., Lupus. 1998; 7 Suppl 2:S126-31; Bevers E M et al., 21: Lupus. 1996 October; 5(5):480-7; Bruckheimer E M et al., J Leukoc Biol. 1996 June; 59(6):784-8; Tomizawa H et al., Pharm Res. 1993 April; 10(4):549-52; Lee K D et al., Biochim Biophys Acta. 1992 Jan. 31; 1103(2):185-97; Palatini P et al., Br J Pharmacol. 1991 February; 102(2):345-50; Utsugi T et al., Cancer Res. 1991 Jun. 1; 51(11):3062-6; Connor J et al. Proc Natl Acad Sci USA. 1989 May; 86(9):3184-8; Fidler I J et al., Biochim Biophys Acta. 1988 Nov. 15; 948(2):151-73; Allen T M et al., Proc Natl Acad Sci USA. 1988 November; 85(21):8067-71; Schroit A J et al., J Biol Chem. 1985 Apr. 25; 260(8):5131-8; Schroit A J et al., Biol Cell. 1984; 51(2):227-38; Rimle D et al., Mol Cell Biochem. 1984 September; 64(1):81-7; Fidler I J et al., Cancer Res. 1980 December; 40(12):4460-6; Poste G et al., Proc Natl Acad Sci USA. 1976 May; 73(5): 1603-7; which are incorporated by reference herein.

This property is exploited in the present invention by using liposomes with relatively high concentrations of PS on their outer layer, to mimic "marked" cells. This enhances the efficiency of delivery of the encapsulated material, e.g., catalase-SKL, which is released in the cytosol and can then move to the peroxisomes.

In another embodiment, liposomes further comprise a protein, or fragment or variant thereof, that possesses fusogenic properties, e.g., a number of viral proteins. Such proteins will be well known to the skilled worker and are discussed, for example, in U.S. Pat. No. 5,916,803; Hughson (1995) *Current Biol.* 5, 265; Iloekstra (1990) *J. Bioenergetics Biomembranes* 22, 675; and White (1990) *Ann. Rev. Physiol.* 52, 675. Conventional methods can be used to attach such proteins or fragments to a liposome.

In a related embodiment, red blood cells or, preferably, red blood cell ghosts may be used as enhanced delivery vehicles into certain cells for the compositions of the invention. See above list of references.

Much of the discussion in this application is directed to modified peroxisome-targeted catalase polypeptides. However, one of skill in the art will recognize that the methods for targeting catalase molecules to peroxisomes can be applied to other molecules as well, and that these targeted molecules can be used in compositions and methods comparable to those described for targeted catalase. The methods of the invention can be used to target any molecule of interest to peroxisomes. In a preferred embodiment, the targeted molecule is one that promotes a reduction of the level of $H_2O_2$ or other ROS in a peroxisome.

In one embodiment of the invention, the targeted molecule comprises any of a variety of small molecules that can modulate the amount of peroxisomal $H_2O_2$. Suitable small molecules, which will be evident to the skilled worker, include, e.g., small organic molecules that inhibit the activity of one or more of the oxidases in a perosixome, or small organic molecules that stimulate the activity of catalase. Methods for attaching the peroxisomal targeting molecules of the invention to such small molecules, as well as methods for testing for their efficacy, are conventional.

In another embodiment, the targeted molecule comprises any of a variety of enzymes other than catalase (or active variants or fragments thereof, as described above for catalase), which reduce the level of peroxisomal hydrogen peroxide. Such enzymes include, e.g., (a) a combination of glutathione reductase and glutathione peroxidase; and (b) a peroxiredoxin.

To effectively reduce ROS in a peroxisome, a glutathione reductase and a glutathione peroxidase must be co-transported into the organelle. Among the suitable glutathione reductases is the human glutathione reductase, which maintains high levels of reduced glutathione in the cytosol. Among the suitable glutathione peroxidases is the human glutathione peroxidase 1, which protects the hemoglobin in erythrocytes from oxidative breakdown.

A variety of peroxiredoxins may be used in the compositions and methods of the invention. These include enzymes from both human and other animal sources. Among the suitable peroxiredoxins are, e.g., the human enzymes:

(1) Peroxiredoxin 1 (Thioredoxin peroxidase 2; Thioredoxin-dependent peroxide reductase 2; Proliferation-associated protein PAG; Natural killer cell enhancing factor A) (NKEF-A)). This enzyme is involved in redox regulation of the cell; it reduces peroxides with reducing equivalents provided through the thioredoxin system but not from glutaredoxin. The enzyme may play an important role in eliminating peroxides generated during metabolism, and might participate in the signaling cascades of growth factors and tumor necrosis factor-alpha by regulating the intracellular concentrations of $H_2O_2$.

(2) Peroxiredoxin 2 (Thioredoxin peroxidase 1; Thioredoxin-dependent peroxide reductase; Thiol-specific antioxidant protein (TSA); PRP; Natural killer cell enhancing factor B (NKEF-B)). This enzyme is involved in redox regulation of the cell; it reduces peroxides with reducing equivalents provided through the thioredoxin system. The enzyme is not able to receive electrons from glutaredoxin. It may play an important role in eliminating peroxides generated during metabolism, and might participate in the signaling cascades of growth factors and tumor necrosis factor-alpha by regulating the intracellular concentrations of $H_2O_2$.

(3) Peroxiredoxin 3 (Thioredoxin-dependent peroxide reductase, mitochondrial precursor; Antioxidant protein (AOP-1); MER5 protein homolog; HBC189; PRX III). This enzyme is involved in redox regulation of the cell. It protects radical-sensitive enzymes from oxidative damage by a radical-generating system.

(4) Peroxiredoxin 4 (Prx-IV; Thioredoxin peroxidase AO372; Thioredoxin-dependent peroxide reductase AO372; Antioxidant enzyme AOE372; AOE37-2). This enzyme is (5) Peroxiredoxin 5 (a,b,c) (peroxiredoxin 5 precursor isoform a, b, or c; antioxidant enzyme B166; TPx type VI; liver tissue 2D-page spot 71B; Alu co-repressor 1 [*Homo sapiens*]). Peroxiredoxin 5 is a member of the peroxiredoxin family of antioxidant enzymes, which reduce hydrogen peroxide and alkyl hydroperoxides. The protein may play an antioxidant protective role in different tissues under normal conditions and during inflammatory processes. This protein interacts with Pex5p. The crystal structure of this protein in its reduced form has been resolved to 1.5 angstrom resolution. The gene encoding peroxiredoxin 5 uses alternate in-frame translation initiation sites to generate mitochondrial or peroxisomal/cytoplasmic forms. Three transcript variants (a, b and c) encoding distinct isoforms have been identified for this gene.

(6) Peroxiredoxin 6 (peroxiredoxin 6; antioxidant protein 2; non-selenium glutathione peroxidase; acidic calcium-independent phospholipase A2; 1-Cys peroxiredoxin [*Homo sapiens*]). Peroxiredoxin 6 is a member of the thiol-specific antioxidant protein family. This protein is a bifunctional enzyme with two distinct active sites. It is involved in redox regulation of the cell; it can reduce $H_2O_2$ and short chain organic, fatty acid, and phospholipid hydroperoxides. It may play a role in the regulation of phospholipid turnover as well as in protection against oxidative injury.

Accordingly, one embodiment of the invention is a molecule, or a combination of two or more molecules, that reduce the level of $H_2O_2$ (and, indirectly, reduce the level of other ROS) in peroxisomes of a cell in need of such treatment, such as an aging cell. For example, such a molecule may comprise an enzyme that participates in the breakdown of $H_2O_2$, or that inhibits the generation of another ROS whose synthesis is dependent on $H_2O_2$, wherein the enzyme is bound to a PTS peptide according to the invention. The enzyme may have a PTS1-type sequence attached at its C-terminus, and/or a PTS2-type sequence attached at or near its N-terminus. In one embodiment, the enzyme is a peroxiredoxin, such as one of the six types of human peroxiredoxin described above. In another embodiment, two molecules may be present: a glutathione reductase and glutathione peroxidase, both of which enzymes comprise a PTS of the invention.

Having now generally described the invention, the same will be more readily understood through reference to the following examples which are provided by way of illustration, and are not intended to be limiting of the present invention, unless specified.

Example I

Materials and Methods

Cell Culture

Early passage IMR90 and Hs27 HDFs, obtained from the National Institutes of Aging, Aging Cell Repository/Coriell Institute for Medical Research (Camden, N.J.) and ATCC (Manassas, Va.), respectively, were cultured in DMEM supplemented with 10% fetal bovine serum (Gibco, Grand Island, N.Y.), penicillin, and streptomycin. The cells were maintained at 37° C. in humidified incubators supplemented with 5% $CO_2$. To achieve higher passage levels, the cells were expanded through sub-cultivation. Late passage cells were confirmed to be at or near replicative senescence by staining for senescence-associated β-galactosidase as described (Dimri et al., 1995).

Where indicated, cells were grown on glass coverslips pretreated with ProNectin F (Biosource International, Camarillo, Calif.).

In Vitro Import Assays

Peroxisomal protein import was examined in semi-permeabilized cells using ELISA- and immunofluorescence-based in vitro assays. Both approaches employed the PTS1(-SKL)-containing substrate protein, luciferase. For the ELISA-system, luciferase was biotinylated and import quantitated either directly in cells or after isolation of cellular/organelles/peroxisomes as described (Terlecky, 2002). A diagrammatic representation of this method is shown in FIG. 2. To ensure that comparisons were being made from equivalent numbers of cells, DNA content was measured and appropriate corrections made in all experiments. The fluorometric method of DNA quantitation was as described by Downs and Wilfinger (1983) except that SYBR® Green (Molecular Probes, Eugene, Oreg.) was used as the DNA-binding dye The immunofluorescence-based import assay was carried out as specifically detailed for IMR90 fibroblasts in Legakis and Terlecky (2001).

To examine the effects of $H_2O_2$ on import, cells were pretreated overnight with 125 μM $H_2O_2$ in serum-containing media, and for 2 h prior to harvest/permeabilization with 250 μM $H_2O_2$ in serum-free media.

Immunocytochemistry/Microscopy

Cells, grown on glass coverslips, were fixed for 10 min in 4% (w/v) paraformaldehyde, treated for 10 min with 10 mM $NH_4Cl$, and permeabilized for 5 min with 1% (v/v) Triton X-100. Cells were blocked for 1 h with 4% (w/v) BSA and incubated with primary antibody for 1 h and secondary antibody for 30-45 min. Rabbit anti-PMP70 (Peroxisomal Membrane Protein of 70 kDa) antibodies were used at a 1/250 dilution, rabbit anti-catalase antibodies were used at a 1/500 dilution, rabbit anti-Pex5p antibodies were used at a 1/500 dilution, and CY3-conjugated goat anti-rabbit antibodies were used at a 1/300 dilution. All reactions were conducted in PBS. Coverslips were mounted using Slowfade antifade (Molecular Probes). A Zeiss LSM-310 confocal microscope was used to obtain all fluorescent images.

For the detection of cellular $H_2O_2$, the method employed was modified from Ohba et al., 1994 and Bass et al., 1983. Here, cells were washed 3× with PBS and treated for 10 min at 37° C. with 25 μM 2',7'-dichlorofluorescin diacetate. The cells were washed again and cellular fluorescence examined by confocal microscopy using an excitation wavelength of 488 nm. Where indicated, early passage Hs27 HDFs were "labeled" by allowing them to endocytose red FluoSphere® microspheres (Molecular Probes). After an overnight incubation, these cells were washed, and seeded onto coverslips containing ("unlabeled") late passage cells. These mixed populations of cells were then examined for the generation of $H_2O_2$.

Enzyme Latency

Latency experiments were as modified from Wanders et al. (1984). Briefly, a confluent 15 cm dish was washed 2× with HBSS, and the cells removed by trypsinization and resuspended in (~10 ml) 10 mM Hepes (pH 7.4), 0.25 M sucrose, 0.1% (v/v) EtOH (Buffer A). The cells were then (i.) pelleted in a clinical centrifuge, (ii.) washed 1× with Buffer A, (iii.) resuspended in Buffer A, and (iv.) aliquoted into appropriate digitonin- and Triton X-100-containing Buffer A reaction solutions. Permeabilization was carried out for 5 min at 4° C., after which the cells were microfuged (2 min) and the resultant supernatants assayed for lactate dehydrogenase or catalase as described (Storrie and Madden, 1990).

Preparation of Plasmids/Proteins

The pGFP-KANL and pDsRed2-SKL mammalian expression vectors were created by adding a 15 nucleotide sequence to the 3' end of GFP in the pEGFP-C3 vector (Clontech, Palo Alto, Calif.), and a 12 nucleotide sequence to the 3' end of DsRed2 in the pDsRed2-C1 vector (Clontech) by PCR amplification. For GFP-KANL, the forward primer, 5'-GTGAAC-CGTCAGATCCGCT-3' (SEQ ID NO: 12), complemented the nucleotide sequence upstream of the GFP ATG start site which contained an Eco47III site. The reverse primer, 5'-CGTctcgagTTA TAGATCAGCTTTCAGCTCGTC-CATGCCGAGAGTA GTCC-3' (SEQ ID NO: 13), complemented the last 22 nucleotides of GFP and created an in-frame 3' end which included nucleotides coding for the peroxisomal targeting signal of catalase, -KANL (underlined), a stop codon, and an XhoI site (lowercase). For DsRed2-SKL, the forward primer, 5'-CCGCTAGCGCTACCGGTCGCCACCATGGCC-3' (SEQ ID NO: 14), complemented the nucleotide sequence upstream of the DsRed2 ATG start site, which contained an Eco47III site. The reverse primer, 5'CGTctcgagTTA TAATTTGGACAGGAACAGGTGGTGGCGGCC-3' (SEQ ID NO: 15), complemented the last 21 nucleotides of DsRed2 and created an in-frame 3' end which included nucleotides coding for the peroxisomal targeting signal -SKL (underlined), a stop codon, and an Xho1 site (lowercase). PCR was performed on a Perkin Elmer GeneAmp PCR System 2400, using Pwo polymerase (Roche, Laval, Canada), yielding fragments that encoded either GFP-KANL or DsRed2-SKL flanked by Eco47III and XhoI sites. The pEGFP-C3 and pDsRed2-C1 vectors were digested using XhoI and Eco47III, resulting in release of the GFP- and DsRed2-containing fragments, respectively. The linearized vectors were then ligated overnight with the appropriate digested PCR fragment, either GFP-KANL or DsRed2-SKL, using T4 DNA Ligase (Roche, Laval, Quebec, Canada). The results were pGFP-KANL, and pDsRed2-SKL, mammalian expression plasmids with GFP-KANL and DsRed2-SKL, respectively, under the control of the CMV promoter. Ligation products were transformed into JM109 bacterial host and plated on LB plates containing 50 μg/ml kanamycin. One transformant of each was selected, amplified, and the (pGFP-KANL and pDsRed2-SKL) plasmids isolated and sequenced (Robarts Research Institute Sequencing Facility) to confirm proper construct sequence. pGFP-SKL was similarly constructed, except that nucleotides coding for the peroxisomal targeting signal -SKL were used instead of those for -KANL.

For use in the Pex5p-binding assays, three (His)$_6$-tagged human catalase proteins differing solely by the identity of their carboxy-terminal residues were expressed in bacteria and purified utilizing Ni-NTA agarose. The recombinant proteins were designed to contain at their carboxy-terminus either (i.) the naturally occurring KANL sequence (KANL), (ii.) an SKL sequence (SKL), or (iii.) no PTS1 sequence at all (−). In the latter case, the KANL sequence was simply deleted. To generate these molecules, the human catalase gene was PCR amplified from a full-length cDNA clone (Invitrogen). The same forward primer was used to amplify each of the three constructs. This nucleotide primer, 5'-ACG-CaggcctGCTGACACGCGGGATCCCGCC-3' (SEQ ID NO: 16) complemented the amino-terminal sequence of human catalase along with a StuI restriction site (lowercase).

Three reverse primers:

(SEQ ID NO: 17)
5'-GGGCGCAAGCTTTCACAGATTTGCCTTGTGCCT-3'

(SEQ ID NO: 18)
5'-GGGCGCAAGCTTTCACAGTTTCGATTTCTCCCTTGCCGCCAAGT-3',
and (SEQ ID NO: 19)
5'-GGCGCAAGCTTTCACTCCCTTGCCGCCAAGTG-3' were designed to produce the KANL, SKL, and "-" versions of catalase, respectively. These primers contained nucleotide changes that coded for the appropriate amino acid substitutions and/or deletions. A HindIII restriction site (lowercase) was also incorporated downstream of the stop codon. Each of the "catalase" genes were amplified by PCR (Eppendorf Mastercycler), digested appropriately, and ligated into pQE30-Xa (Qiagen). Ligation products were transformed into the E. Coli strain DH5α, and recovered plasmids were confirmed to be correct by restriction analysis and DNA sequencing. The sequence-verified (His)$_6$-tagged human catalase constructs were then expressed and purified according to the manufacturer's instructions (Qiagen).

Nuclear Microinjection and Imaging

Early and late passage Hs27 cells grown on glass coverslips were microinjected on a Leitz Labovert FS equipped with a microinjector. Glass capillary needles (World Precision Instruments, Sarasota, Fla.) were prepared with a Kopf Vertical Pipette puller. Plasmids were diluted to 15 μg/ml in an injection buffer consisting of 100 mM KCl and 20 mM KH$_2$PO$_4$ (pH 7.4). Cells were nuclear injected with either the pGFP-SKL or the pGFP-KANL and incubated for 18 or 45 h. Live fluorescence images of microinjected cells were collected on a Zeiss Axiovert S100 inverted microscope equipped with an FITC filter set and a CCD camera. Images were processed using SensiCam imaging software (PCO CCD Imaging).

When pGFP-KANL and DsRed2-SKL were nuclear microinjected simultaneously into late passage HDFs, they were added at a concentration of 20 μg/ml and 15 μg/ml, respectively. These cells were grown on glass coverslips, microinjected, and fixed 42 h later. After mounting on glass slides, the cells were imaged on a Zeiss Axioplan2 microscope.

Pex5p Binding Assays

Human Pex5p was isolated as a glutathione S-transferase fusion protein from E. coli as described (Amery et al., 2001). Proteins (obtained from Sigma) were coated onto microtiter well strips (Maxisorp Immunomodule, Nunc) overnight in 50 mM sodium carbonate (pH 9.0). (Equivalent coating of proteins in microwells was confirmed by the Bio-Rad protein assay performed in situ.) The wells were washed 2× with PBS, and blocked for 4 h at 30° C. with 10 mg/ml nonfat milk in PBS plus 0.05% (v/v) Tween-20. The wells were washed again and incubated overnight with 1.6 μg GST-HsPex5p in PBS. To determine the amount of GST-Pex5p bound, the wells were washed, and incubated with rabbit anti-GST antibodies (dilution 1:2500) followed by peroxidase-labeled goat anti-rabbit antibodies (dilution 1:2500). After washing, the wells were developed and stopped as described (Smythe et al., 1992; Terlecky, 2002). A microplate reader was used to determine the absorbance at 490 nm.

Pex5p ligand blots were carried out as described in Fransen et al., 1998, with the following changes. Here, no methionine was used in the reaction buffer and the ligand was GST-Pex5p. Also, after the binding and washing steps, GST-Pex5p was detected with rabbit anti-GST antibodies (1:2500) and peroxidase-labeled goat anti-rabbit Ig secondary antibodies (1:2500).

Immunoprecipitation/Protease Protection

Immunoprecipitation and protease protection experiments were performed on organelles from IMR90 fibroblasts. To prepare them, equivalent numbers of cells (confirmed by DNA content measurements—as above) were washed with HBSS, harvested in homogenization buffer (10 mM ethanolamine (pH 7.8), 10 mM acetic acid, 1 mM EDTA, 0.1% EtOH, 0.25 M sucrose) with a rubber policeman, and disrupted by passage through a narrow gauge needle followed by Dounce homogenization. Nuclei and unbroken cells were removed by centrifugation at 1000×g for 10 min at 4° C. and organelles isolated by centrifugation at 10,000×g for 20 min at 4° C. (The latter step quantitatively pellets PMP70/peroxisomes from these cells.) For immunoprecipitation the organelles were lysed with a modified RIPA buffer (50 mM Tris/HCl (pH 7.4), 150 mM NaCl, 1% (v/v) NP40, 0.5% (v/v) deoxycholate, 0.1% (w/v) SDS) plus protease inhibitors (complete cocktail—Sigma), and anti-Pex5p (or preimmune) antibodies added. After 2 h at 4° C. on a rotator, protein A sepharose (Sigma) was added for 30 min at 4° C. The immunoprecipitate was collected by centrifugation, washed, and run on a 10% SDS-PAGE gel. After transfer to nitrocellulose, the blots were probed with anti-Pex5p antibodies followed by chemiluminescent secondary antibodies (KPL, Gaithersburg, Md.).

When protease treated, the organelles were incubated with 50 µg/ml proteinase K (Sigma) for 30 min on ice. The reaction was terminated by the addition of 2 mg/ml phenylmethylsulfonylfluoride. SDS-PAGE sample buffer was then added to the samples and the proteins separated on a 10% gel. After transfer to nitrocellulose, immunoblots were performed with anti-Pex5p or anti-catalase antibodies as above. Where indicated, organelles were disrupted with 1% Triton X-100 prior to protease treatment.

Example II

Age-Related Decline in PTS1-Import Efficiency

Biochemically-defined in vitro assays were used to show that peroxisomal PTS1-protein import is reduced in aging cells (FIG. 1). The cells employed in this analysis, either IMR90 or Hs27 HDFs, were serially passaged to achieve appropriate population doubling levels (PDLs). A cell's PDL may be considered akin to its age (for reviews see Beckman and Ames, 1998; Dice, 1993), and for our purposes here, we define (IMR90) early passage cells as PDL 1-35, middle passage cells as PDL 36-45, and late passage cells as PDL 46-60. IMR90 cells reach replicative senescence at ~PDL60. Hs27 cells, which senesce at comparable passage numbers, were similarly analyzed at early, middle, and late passage. Interestingly, both cell types showed import deficits beginning in middle passage (FIG. 1).

The import substrate in these assays was luciferase, a PTS1-protein containing the carboxy-terminal sequence, serine-lysine-leucine (Gould et al., 1987). In FIGS. 1, A and B, we utilized a biotinylated version of this substrate and an ELISA-based quantitative assay to evaluate import. This assay employs semi-permeabilized cells, and measures the accumulation of biotinylated-luciferase inside peroxisomes (Terlecky et al., 2001; Terlecky, 2002). After the transport reaction, biotin groups on unimported substrates are blocked, and import assessed either in organelles prepared by cellular homogenization and fractionation (FIG. 1A) or in (lysed) cells (FIG. 1B). Irrespective of the cell type or assay variation employed, PTS1-protein import was reduced by up to 60% in late passage HDFs. Qualitatively similar results were obtained using an immuno-fluorescence-based import assay (Wendland and Subramani, 1993; Rapp et al., 1993) in which cells are semi-permeabilized with streptolysin-O, and the peroxisomal accumulation of luciferase determined. The number of detectable peroxisomes was determined by counting immunoreactive structures in each of the cells. In early passage cells, the average number/cell was about 160, in middle passage cells, about 40, and in later passage cells, about 170. With this system, import appears even more dramatically affected in middle passage cells, perhaps reflecting the threshold nature of the assay. That is, the immunofluorescence signal obtained is largely all-or-none; import reduced below a certain critical level will simply not be detected.

Example III

Characteristics of Peroxisomes in Aging Cells

Peroxisomes of early, middle, and late passage HDFs were examined by indirect immunofluorescence microscopy. The organelles, identified by their reactivity with antibodies to the peroxisomal membrane protein of 70 kDa (PMP70), appeared as randomly scattered punctate structures in early passage cells. In middle and late passage cells, the number of these structures increased. To more carefully document this point, we counted the number of immunoreactive structures per unit area in early, middle, and late passage IMR90 cells. We found that for every one such structure in early passage cells, there were 1.6 in middle passage cells, and 2.2 in late passage cells. Similar results were obtained with Hs27 cells. Furthermore, this increase in peroxisome abundance was also observed with antibodies to the membrane peroxin, Pex 14p.

To compare early and late passage cells more directly, we analyzed peroxisomal markers in co-cultured cells. For these experiments, early and late passage HDFs were sub-cultivated onto the same culture dishes and coverslips prior to immunostaining. (The identity of late passage cells was confirmed by staining with the histochemical biomarker, senescence-associated β-galactosidase) Once again after staining with antibodies to PMP70, differences in peroxisome number and form were manifest in cells of distinct ages.

Peroxisomal matrix proteins were also examined by immunocytochemistry in co-cultured cells. Two antibodies were used for this purpose; those generated to catalase and those specific for a peptide containing the carboxy-terminal PTS1 sequence, serine-lysine-leucine. Both antibodies recognized punctate structures in early passage cells. In late passage cells, however, the staining was noticeably different; in IMR90s, both matrix markers appeared less intense, with a considerable amount of diffuse, cytosolic staining. The behavior of peroxisomal matrix markers in late passage cells was also more variable. In Hs27s, for example, some old cells catalase appeared in distinct, peroxisomal structures, but also in the cytosol. In others, the staining was more completely cytosolic. These results suggest that at least a portion of cellular catalase and other PTS1-containing enzymes are mislocalized in late passage cells.

To investigate this point further, we performed latency analysis (FIG. 2). In this assay, early and late passage (IMR90) cells were treated with increasing concentrations of digitonin and the release of (cytosolic) lactate dehydrogenase and (peroxisomal) catalase was measured enzymatically. At 100 μg/ml digitonin, lactate dehydrogenase was almost completely released in early passage cells. (A similar profile was obtained with late passage cells, but is not shown for clarity.) This concentration establishes the point at which the plasma membrane was compromised and access to the cytosolic compartment was afforded. At this, and greater concentrations of digitonin, the relative amount of detectable catalase was significantly higher in the late passage cells, confirming the mislocalization suggested by immunofluorescence. Note that complete release of catalase was only realized in buffers supplemented with Triton X-100.

Example IV

Catalase Contains a Weak PTS1 which Interacts Poorly with Pex5p

The import of PTS1-proteins containing the prototypical serine-lysine-leucine carboxy-terminus is clearly compromised in aged cells (See, e.g., FIG. 1). Catalase, which contains a divergent PTS1, specifically, lysine-alanine-asparagine-leucine, also shows age-related declines in its import efficiency (See, e.g., FIG. 2). To investigate whether or not one of these signals is more significantly impacted than the other, we nuclear microinjected plasmids encoding the green fluorescent protein coupled either to serine-lysine-leucine (GFP-SKL), or lysine-alanine-asparagine-leucine (GFP-KANL), into early and late passage HDFs. Live cells were then examined for the expression of the hybrid proteins 18 and 45 b later under a fluorescent microscope.

GFP-SKL was efficiently imported in early passage cells, accumulating in peroxisomes by 18 h. In late passage cells, import was delayed, with solely faint fluorescent structures appearing at 18 h. Only by 45 h did GFP-SKL appear to have been imported to a significant extent. GFP tagged with the catalase PTS1, GFP-KANL, did not appear in peroxisomes of early passage cells until 45 h after microinjection, and did not accumulate at all at 45 h in peroxisomes of late passage cells. In old cells, it took some 115 h before import of GFP-KANL was finally detected.

We also examined the import of reporters containing the two PTS1 sequences in the same (senescent) cell. In this experiment, DsRed2 was coupled to serine-lysine-leucine (DsRed2-SKL), and GFP was coupled to lysine-alanine-asparagine-leucine (GFP-KANL). Note how 42 h after microinjection, DsRed2-SKL appeared in peroxisomes, whereas GFP-KANL remained largely in the cytosol. Clearly, aging compromises the peroxisomal protein import apparatus, with the PTS of catalase particularly affected.

Import of PTS1-containing proteins is mediated by Pex5p, a soluble receptor molecule which shuttles between the cytosol and the organelle (Dammai and Subramani, 2001; Dodt and Gould, 1996). Pex5p's functional cycle commences with the binding of its cargo in the cytosol. A potential explanation for differences in the import efficiencies of two PTS1-containing proteins is dissimilar recognition by Pex5p at this step. To determine if Pex5p displayed preferential interaction with proteins containing a serine-lysine-leucine PTS1, e.g. luciferase, versus those containing a lysine-alanine-asparagine-leucine PTS1, e.g. catalase, we performed solid phase and ligand blot binding assays (FIGS. 3A-3F). In the former, luciferase, catalase and two control proteins (bovine serum albumin and ovalbumin) were coated onto the wells of microplates and the binding of GST-tagged human Pex5p examined. Our results indicate that Pex5p's binding to luciferase was consistently 3 to 4× higher than to catalase (see representative experiment shown in FIG. 3A). Only little binding was observed to the control proteins (FIG. 3A), and no binding was detected in experiments conducted with (i.) no Pex5p added, (ii.) no proteins coated, (iii.) or heat denatured Pex5p. Similar results were obtained with ligand blots, in which luciferase, catalase, and bovine serum albumin were separated by SDS-PAGE, transferred to nitrocellulose, and blotted with Pex5p. Once again, the binding of Pex5p to luciferase was dramatically higher than to the other proteins tested (FIGS. 3B, 3C).

We also addressed this point by examining binding of Pex5p to purified recombinant human catalase molecules differing only by the identity of their carboxy-terminal residues. In this experiment, catalase molecules were engineered to contain a poly-histidine tag (for purification) and either their own PTS1 (KANL), an altered PTS1 (SKL), or no PTS1 (−). After expression, purification, and characterization (FIGS. 3D, 3E), the three species were blotted with Pex5p. As shown in FIG. 3F, Pex5p preferentially binds catalase with the "SKL" PTS1.

Example V

Pex5p Cycling

As part of its "extended shuttle" to the peroxisome, Pex5p and bound cargo interact with docking proteins on the organelle's membrane. This interaction is transient; accumulation of the receptor at the peroxisome membrane is associated with errors in the cycling mechanism and a resultant reduction in protein import (Dodt and Gould, 1996). To examine whether or not aberrant Pex5p cycling was associated with aging cells, we analyzed the level of peroxisome-associated Pex5p. To accomplish this, we isolated organelles, which were normalized to equal amounts of PMP70, from HDFs at different ages, and immunoprecipitated Pex5p (FIGS. 4A-4D). Importantly, the level of membrane-associated Pex5p was consistently higher in middle and late passage cells. Control experiments revealed that the total amount of cellular Pex5p did not change in these cells, only the amount associated with organelle membranes was altered. Immunostaining of Pex5p in cells confirmed this age-related increase in peroxisome-association.

Recently, Pex5p was shown to actually enter the peroxisome as part of its reaction cycle (Dammai and Subramani, 2001). To determine if the peroxisome-associated Pex5p observed in late passage cells was on the membrane or inside the organelle, we performed a protease-protection assay (FIG. 4E). In this experiment, organelles from late passage cells were treated with proteinase-K and immunoblotted. Our results indicate that Pex5p was completely degraded by the protease, under conditions in which the luminal enzyme, catalase, was largely insensitive. Importantly, Pex5p and catalase were both completely degraded by the protease when the organelles were pretreated with detergent. Taken together, these results suggest that aging cells accumulate Pex5p on the surface of their peroxisomes. It should be noted that Pex5p also appears on the surface of peroxisomes (and is largely protease sensitive) in early passage cells, presumably reflecting normal trafficking of the PTS1 import receptor.

Example VI

Role of Hydrogen Peroxide in Peroxisome Senescence

A potential consequence of peroxisomes exhibiting a reduced capacity to import enzymes is a loss of homeostatic regulation. That is, perhaps there is an alteration in the balance between those peroxisomal enzymes that generate $H_2O_2$ and other ROS, and those, like catalase, which degrade the toxic metabolites. One manifestation of such a disequilibrium would be a build-up of $H_2O_2$ in cells. To analyze this, we treated HDFs of various ages with the oxidation-sensitive dye, 2',7'-dichlorofluorescin diacetate (Bass et al., 1983; Ohba et al., 1994). This compound enters cells and is converted to a non-fluorescent, cell-impermeant derivative. Exposure to $H_2O_2$ converts the compound to the fluorescent version, 2',7'-dichlorofluorescein, which is readily visualized by confocal microscopy. Little $H_2O_2$ was seen in early and middle passage cells. However, in late passage cells, a dramatic increase of the ROS appeared. Similar results were obtained when this assay was performed with co-cultured early and late passage HDFs. Also, treatment of early passage HDFs with the catalase inhibitor, aminotriazole, resulted in an induction of $H_2O_2$ very similar to that seen in late passage cells. Thus, although our studies certainly support the idea that peroxisomes may contribute to the production of $H_2O_2$ in late passage cells, the extent of this contribution remains an important open question. Also not entirely clear is why $H_2O_2$ accumulates largely in late passage cells, despite the fact that peroxisomal protein import is already impaired in middle passage cells (FIG. 1). Perhaps this reflects the involvement of glutathione peroxidase or other cytosolic $H_2O_2$-degrading activities whose capacity to process the ROS are eventually overwhelmed in late passage cells.

The relationship between cellular accumulation of $H_2O_2$ and the induction of a senescent phenotype has already been established. Specifically, Chen and Ames (1994) showed that HDFs treated with sub-lethal doses of $H_2O_2$ displayed many characteristics of senescent cells, including growth arrest, reduced activity of critical cellular enzymes, and an "aged" morphology. We addressed a slightly different question in FIG. 5, by testing whether or not exposing early passage cells to $H_2O_2$ would induce "peroxisome senescence"—and effect a reduced ability of the organelle to import its constituent enzymes. Our results suggest this is the case, as $H_2O_2$ treatment of cells significantly reduced PTS1-protein import (FIG. 5). Furthermore, these cells accumulated Pex5p on their peroxisomes as determined by immunofluorescence, and immunoprecipitation. In sum, these results suggest that $H_2O_2$ amasses in aging cells and that such accumulation may contribute to a reduction in the functional integrity of peroxisomes. These phenomena presumably contribute not only to the "aging" of peroxisomes, but to cellular aging as well.

Example VII

Additional Studies of Catalase Import into Peroxisomes

Subsequent studies were directed to understanding the molecular mechanisms of peroxisomal protein import and organelle biogenesis in human health and aging. As shown above, the peroxisome import apparatus is compromised by age—with the enzyme catalase particularly affected. Peroxisomes generate $H_2O_2$ as a by-product of a number of oxidation reactions carried out in the organelle. One consequence of a reduced catalase concentration within the peroxisome is the potential for an accumulation of $H_2O_2$, a potentially toxic ROS. The results suggested that aging cells do indeed produce elevated levels of $H_2O_2$ and that this may have contributed to further reductions in the import capacity of the organelle. Also, this loss of the balance between peroxisomal pro- and antioxidants may also contribute to cellular aging.

The present inventors previously observed that peroxisomes in aging human cells, although unable to efficiently import their constituent enzymes, nevertheless appear more numerous. The mechanisms that regulate peroxisome biogenesis may have become disabled so that the organelle divides in the absence of significant protein import. This observation was extended by examining early and late passage cells by electron microscopy. Late passage ("old") fibroblast clearly contain a plethora of small vesicles interpreted as being the peroxisomes seen by immunofluorescence analysis. At least a portion of these vesicles become immuno-decorated by antibodies specific for peroxisomal membrane protein 70 (PMP70) and gold-labeled secondary antibodies.

As discussed above, a senescence-accompanying deficit in protein import would result in impaired peroxisomal "function". That is, that the activity of certain peroxisomal enzymes would be compromised—either due to their reduced import or perhaps due to inactivation by accumulated $H_2O_2$. This issue was addressed using an assay to measure dihyroxy-acetone-phosphate acyltransferase (DHAP-AT), the enzyme responsible for catalyzing the first step in ether-phospholipid biosynthesis. The results indicate that late passage cells exhibit reduced activity of this critical enzyme, leading to the prediction that peroxisomes of late passage cells will contain reduced levels of membrane plasmalogens—the ultimate product in the enzymatic cascade initiated by DHAP-AT. The effect of reduced plasmalogens in peroxisome and/or other cellular membranes would be profound since plasmalogens exert protective effects against various toxic insults. The DHAP-AT enzyme itself contains both PTS1 and PTS2 components—that is, it is a heterodimer. This is supported by the observations that deficits in either PTS1 import (e.g., in cells of Zellweger syndrome patients) or PTS2 import (in cells of rhizomelic chondrodysplasia punctata patients) results in significantly reduced DHAP-AT levels.

To extend our published observations that catalase is a relatively poor import substrate both in early and late passage cells, in vitro import assays were conducted and results appear in FIG. 6 (and continued in FIGS. 8 and 9). Specifically, catalase import is reduced in late passage human cells—in keeping with Examples I-VI, supra, which show mislocalization of the enzyme in these cells. Again, catalase contains a non-canonical PTS1 (-KANL) at its C-terminus. Studies based on a ligand blotting approach showed that catalase with a re-engineered C-terminus, namely with an -SKL peptide present, effected a more robust interaction with the PTS1-import receptor, Pex5p. As described herein, these observations were extended using surface plasmon resonance (SPR) with a BIACORE biosensor 3000 (FIG. 7). These results support what was previously observed—catalase with its naturally occurring PTS1 is poorly recognized as compared to a version of the molecule containing the -SKL PTS1. Although only a single concentration is shown, extensive "kinetic" analyses have permitted calculation of on-rates, off-rates, and $K_D$ values.

Another experiment compared the import efficiencies of the (-SKL)-containing enzyme, luciferase, and catalase in vitro. As shown in FIG. 8, luciferase is a far more robust substrate than catalase for the peroxisomal import apparatus, an effect compounded by the aging of cells.

One prediction from these results is that catalase engineered to contain an -SKL PTS1 will be imported more efficiently that the naturally occurring -KANL-containing enzyme. FIG. 9 confirms this prediction; catalase with the "strong" PTS1 is imported to a far greater extent. These experiments were performed with human (A431) cells, a commonly used cell line. Similar results are obtained in human fibroblasts.

The more efficient import of catalase by virtue of this altered (PTS1) targeting signal serves as the basis for the present inventors' strategy to alter the course of peroxisome decline. Catalase "reintroduced" into the peroxisome will result in a cell that produces manageable levels of $H_2O_2$ and that experiences reduced effects of accumulation of this and other toxic ROS.

For efficient introduction of catalase into cells, the present inventors utilize a a "protein transduction" strategy as described Morris and colleagues (*Nature Biotechnology*, 19, 1173-1176, 2001). The basis of this procedure is that a specially designed 21 amino acid peptide (called Pep1 or Chariot™) will adsorb to a protein of interest, here catalase, in an initial binding step. This peptide/catalase complex is then added to cells in the transduction phase of the procedure. The complex is transduced across the plasma membrane and accesses the cell cytoplasm at which time the complex dissociates. Catalase is now free to engage the peroxisomal import apparatus and be imported into the organelle.

First, using the easily visualized reporter protein, β-galactosidase, the present inventors showed protein transduction into human fibroblasts. Importantly, endocytosis cannot explain these results as the cells were still blue (indicating the presence of cellular β-galactosidase) when the experiment was performed at 4° C. or in the absence of ATP.

Next, catalase was delivered into cells with this technique (FIG. 10). These experiments, relied upon acatalasemic fibroblasts—cells that express only a small amount of catalase (compare levels of immunoreactive catalase in cells labeled "Acat" versus normal "IMR90" fibroblasts). However, upon transduction, catalase levels were significantly increased in (Acat) cells. If a His-tagged version of catalase was used— this larger molecule was transduced was present as a slightly slower migrating (immunoreactive) species. Although the catalase in this study had its own PTS1 in these experiments, other results suggest that the —SKL-tagged version of the molecule is similarly transduced.

The present inventors previously showed that late passage fibroblasts produced elevated levels of $H_2O_2$ as compared to early passage cells. Here it was demonstrated that acatalasemic fibroblasts also produced very high levels of $H_2O_2$, levels that were considerably higher than in, for example, early passage IMR90 cells. Importantly, transduction of catalase into these cells dramatically reduced the $H_2O_2$ content. Numerous cells examined in this way permitted a quantitative analysis. Importantly, the amount of $H_2O_2$ in cells was reduced by some 50% in this experiment. One should keep in mind that these acatalasemia cells do not make normal amounts of catalase. Nevertheless, there was no previous evidence that such cells have import defects per se. Therefore, these cells should not be considered "aged" and would be expected to import catalase, even with its own "weaker" PTS1.

Studies are performed in which catalase is engineered to include a strong targeting signal (SKL) and is introduced into a late passage cell. Such catalase reduces cellular $H_2O_2$. Further, introducing catalase-SKL into early passage cells delays (or eliminates) the onset of senescence.

Example VIII

In Vivo Studies of Catalase-SKL Treatment of Mammals

"Protein Transduction" is a relatively new form of introducing biologically relevant polypeptides into cells and tissues of animals, as studied in mice. See, for example, "*In Vivo Protein Transduction: Delivery of a Biologically Active Protein into the Mouse*" (Science, 1999, 285:1569-1572).

Accordingly, a study is conducted to introduce catalase-SKL into a live organism. The procedure is as follows. A protein transduction domain from the HIV-Tat protein (described above) is fused at the N-terminus of catalase-SKL. A poly-histidine affinity tag (His-Tag) is engineered into the molecule (Group A). As one control (Group B), native catalase is similarly fused to the HIV-Tat domain with a His-Tag. In another control (Group C), a native catalase from which the PTS sequence has been removed is fused to the HIV-Tat domain with a His-Tag. Additional controls include Group D, an unrelated protein of similar molecular mass but devoid of catalase enzymatic activity, including human serum albumin, fused and handled in the same way and linked to SKL.

The fusion proteins are isolated by Ni-chromatography based on the binding of the poly-histidine sequence to the metal atoms. The isolated fusion proteins are then denatured, and injected intraperitoneally into separate groups of mice at doses of 10 μg-1 mg per mouse (0.1 mg-10 mg/Kg).

After intervals of 2-4 hours, the biodistribution and the activity of the injected proteins is measured. Biodistribution is measured by enzymatic assays of each tissue of interest. Total cellular catalase activity is found to increase in groups A, B and C, but not D. The increase in Group A is greatest. The amount and enzymatic activity of catalase present in peroxisomes obtained from liver, fibroblast, lung, heart, brain, spleen and kidney cells/tissues taken from the treated mice is measured. Group A has markedly more catalase protein as well as catalase enzymatic activity than Groups B and C. Group D shows presence of the serum albumin protein in peroxisomes, but, of course, no increase in catalase enzymatic activity.

The presence of transduced catalase protein can be distinguished from the endogenous catalase enzyme by virtue of its size (slightly larger than the endogenous form) as well as by its reactivity with anti-His antibodies or Ni-HRP cytochemical staining reagents.

The biodistribution study confirms that measurable quantities of the catalase and Group D proteins reach virtually all of the tissues examined.

On the basis of the foregoing, studies are designed to determine the following parameters and the following results are obtained:

(1) more animals receiving catalase-SKL are resistant to oxidative stress than are controls (To quantitate this effect, cells and/or organisms are treated with the oxidative stress inducer paraquat, and damage to proteins, DNA and lipids is assessed. Stress markers, including Hsp70 family members, are measured. Furthermore, intercellular levels of (a) oxidized proteins (measured by examining the degree of carbonyl modification of proteins) and (b) plasmalogens are determined; and oxidative damage to DNA is measured.);

(2) as the mice age, their ability to import the infused native catalase falls relative to their ability to import infused catalase-SKL;
(3) in animals treated chronically (once a week or every other week) with catalase-SKL (vs controls):
  (i) peroxisomes and other cellular organelles and biochemical processes maintain a "younger" level of structure and function;
  (ii) the expression profile of genes whose expression is known to be associated with aging more closely resembles that of younger animals;
  (iii) measures of "quality of life" (e.g., immune function, libido, appetite, physical activity etc.) and cognitive function are improved.
(4) animals treated chronically (once a week or every other week) with catalase-SKL (vs controls) live and longer—their life span is increased by about 30%.

Discussion of Examples

The peroxisome is a ubiquitous organelle of nucleated cells. Its role in various physiological processes, including lipid metabolism and specific steps of cholesterol, bile acid, and plasmalogen biosynthesis make it indispensable for human health. The organelle carries out a form of respiration, with its oxidases producing $H_2O_2$ as an end product. This highly poisonous ROS is rapidly converted to water through the action of peroxisomal catalase, at least under most circumstances. As human cells age, the peroxisome's ability to maintain this balance of $H_2O_2$-generating and -degrading activities and to prevent oxidative stress is compromised contributing to the cellular aging process. The present inventors have characterized peroxisomes in aging HDFs, and provide an explanation for how this state of lost equilibrium and reduced organelle function arises.

Peroxisomes import enzymes posttranslationally from the cytosol (Lazarow and Fujiki, 1985). Age-related changes in the organelle's import efficiency were examined as described above The results indicated that human peroxisomes import an SKL-containing PTS1-reporter less efficiently with advancing age. PTS1 is a name given to a class of peptide sequences that direct proteins to the peroxisome. All PTS1-containing enzymes are thought to engage the cycling receptor, Pex5p, as part of their transport mechanism. Catalase contains a PTS1, but one that is considerably different from all others. Appending its PTS1 to GFP resulted in a fusion protein that was (a) less efficiently imported than a serine-lysine-leucine-tagged GFP reporter in early passage cells, and (b) considerably less well imported than the other reporter in late passage cells. These results again confirmed that catalase is a relatively poor substrate for the peroxisomal protein import apparatus (Lazarow et al., 1982). In more recent studies, two fibroblast cell lines have been isolated from patients with Zellweger-like disorders, in which the import of catalase is selectively compromised (Sheikh et al., supra). "Catalase-less peroxisomes" have also been described in a patient with infantile Refsum's disease (Fujiwara et al., 2000).

As for the question of why catalase is imported less efficiently even in early passage cells—and why the effect is exacerbated in late passage cells, the answer to be the first question appears to be due, in part, to the fact that Pex5p only poorly recognizes catalase.

The present studies identified at least one critical mechanistic step that is affected in aging cells—that of Pex5p cycling. It appears certain that the accumulation of oxidatively damaged macromolecules plays a role in cellular senescence and is an important determinant of organismal longevity (Lee and Wei, 2001; Johnson et al., 1999; Beckman and Ames, 1998). A number of degenerative diseases may also be linked to ROS-induced alterations in cellular functions (Masters and Crane, 1995). According to the present invention, the peroxisome, an organelle vital to lipid and membrane biosynthesis and functioning, is a contributor to the oxidative load experienced by aging cells. The organelle converts nearly all of the molecular oxygen it consumes to $H_2O_2$ (Singh, 1996). Coupled with estimates of hepatic peroxisomes consuming 10% or more of total cellular oxygen, it is clear that this is a significant amount of ROS under consideration. The peroxisome's reduced capacity to import PTS1-containing enzymes—especially catalase, creates functionally compromised organelles in aging cells that do not efficiently metabolize $H_2O_2$— with serious potential consequences. Accumulated $H_2O_2$ adds to oxidative stress and damages cellular constituents. Finally, the effects of $H_2O_2$ actually may further decrease the efficiency of peroxisomal matrix protein import and result in a self-perpetuating negative spiral. Importantly, this spiral may be acting early, before any obvious characteristics of aging are observed and may contribute to the initial stages of peroxisome dysfunction and cellular senescence. Thus, the present compositions and methods, designed to counteract such a spiral, add an important component to our capacity to combat some of the effects of aging.

DOCUMENTS CITED ABOVE

Amery, L., Sano, H., Mannaerts, G. P., Snider, J., Van Looy, J., Fransen, M., and Van Veldhoven, P. P. (2001). Identification of Pex5p-related novel peroxisome targeting signal 1 (PTS1)-binding proteins in mammals. Biochem. J. 357, 635-646.

Bass, D. A., Parce, J. W., Dechatelet, L. R., Szejda, P., Seeds, M. C., and Thomas, M. (1983). Flow cytometric studies of oxidative product formation by neutrophils: A graded response to membrane stimulation. J. Immunol. 130, 1910-1917.

Beckman, K. B., and Ames, B. N. (1998). The Free Radical Theory of Aging Matures. Physiol. Rev. 78, 547-581.

Chen, Q., and Ames, B. N. (1994). Senescent-like growth arrest induced by hydrogen peroxide in human diploid fibroblasts. Proc. Natl. Acad. Sci. USA 91, 4130-4134.

Dammai, V., and Subramani, S. (2001). The human peroxisomal targeting signal receptor, Pex5p, is translocated into the peroxisomal matrix and recycled to the cytosol. Cell 105, 187-196.

Dice, J. F. (1993). Cellular and molecular mechanisms of aging. Physiol. Rev. 73, 149-159.

Dimri, G., Lee, X., Basile, G., Acosta, M., Scott, G., Roskelley, C., Medrano, E. E., Linskens, M., Rubelj, I., Pereira-Smith, O., Peacocke, M., and Campisi, J. (1995). A biomarker that identifies senescent human cells in culture and in aging skin in vivo. Proc. Natl. Acad. Sci. USA 92, 9363-9367.

Dodt, G., and Gould, S. J. (1996). Multiple PEX genes are required for proper subcellular distribution and stability of Pex5p, the PTS1 import receptor: evidence that PTS1 protein import is mediated by a cycling receptor. J. Cell Biol. 135, 1763-1774.

Downs, T. R., and Wilfinger, W. W. (1983). Fluorometric quantification of DNA in cells and tissue. Anal. Biochem. 2, 538-547.

Fransen, M., Terlecky, S. R., and Subramani, S. (1998). Identification of a human PTS1 receptor docking protein directly required for peroxisomal protein import. Proc. Natl. Acad. Sci. USA 95, 8087-8092.

Fujiwara, C., Imamura, A., Hashiguchi, N., Shimozawa, N., Suzuki, Y., Kondo, N., Imanaka, T., Tsukamoto, T., and Osumi, T. (2000). Catalase-less peroxisomes. Implication in the milder forms of peroxisome biogenesis disorder. J. Biol. Chem. 275, 37271-37277.

Gould, S. J., Keller, G., and Subramani, S. (1987). Identification of a peroxisomal targeting signal at the carboxy terminus of firefly luciferase. J. Cell Biol. 105, 2923-2931.

Gould, S. J., and Valle, D. (2000). Peroxisome biogenesis disorders. Genetics and Cell Biology. TIG 16, 340-345.

Harano, T., Nose, S., Uezu, R., Shimizu, N., and Fujiki, Y. (2001). Hsp70 regulates the interaction between the peroxisome targeting signal type 1 (PTS1)-receptor Pex5p and PTS1. Biochem. J. 357, 157-165.

Hayflick, L. (1965). The limited in vitro lifetime of human diploid cell strains. Exp. Cell Res. 37, 614-636.

Horiguchi, H., Yurimoto, H., Goh, T.-K., Nakagawa, T., Kato, N., and Sakai, Y. (2001). Peroxisomal catalase in the methylotrophic yeast *Candida boidinii*: Transport efficiency and metabolic significance. J. Bacteriol. 183, 6372-6383.

Ito, R., Huang, Y., Yao, C., Shimozawa, N., Suzuki, Y., Kondo, N., Imanaka, T., Usuda, N., and Ito., M. (2001). Temperature-sensitive phenotype of Chinese hamster ovary cells defective in Pex5 gene. Biochem. Biophys. Res. Commun. 288, 321-327.

Johnson, F. B., Sinclair, D. A., and Guarente, L. (1999). Molecular biology of aging. Cell 96, 291-302.

Lazarow, P. B., and Fujiki, Y. (1985). Biogenesis of peroxisomes. Ann. Rev. Cell Biol. 1, 489-530.

Lazarow, P. B., Robbi, M., Fujiki, Y., and Wong, L. (1982). Biogenesis of peroxisomal proteins in vivo and in vitro. In Peroxisomes and Glyoxysomes, Kindl, H. and Lazarow, P. B., eds. (Annals of the New York Academy of Sciences, Volume 386, New York, N. Y.), pp. 285-300.

Lee, C.-K., Klopp, R. G., Weindruch, R., and Prolla, T. A. (1999). Gene expression profile of aging and its retardation by caloric restriction. Science 285, 1390-1393.

Lee, H.-C., and Wei, Y.-H. (2001). Mitochondrial alterations, cellular response to oxidative stress and defective degradation of proteins in aging. *Biogerontology* 2, 231-244.

Legakis, J. E., and Terlecky, S. R. (2001). PTS2 protein import into mammalian peroxisomes. Traffic 2, 252-260.

Li, X., and Gould, S. J. (2002). PEX11 promotes peroxisome division independently of peroxisome metabolism. J. Cell Biol. 156, 643-651.

Masters, C. J., and Crane, D. I. (1999). On the role of the peroxisome in ontogeny, ageing and degenerative disease. Mech. Ageing Dev. 80, 69-83.

Ohba, M., Shibanuma, M., Kuroki, T., and Nose, K. (1994). Production of hydrogen peroxide by transforming growth factor-$\beta$1 and its involvement in induction of egr-1 in mouse osteoblastic cells. J. Cell Biol. 126, 1079-1088.

Purdue, P. E., and Lazarow, P. B. (2001). Peroxisome biogenesis. Annu. Rev. Cell Dev. Biol. 17, 701-752.

Purdue, P. E., and Lazarow, P. B. (1996). Targeting of human catalase to peroxisomes is dependent upon a novel COOH-targeting sequence. J. Cell Biol. 134, 849-862.

Rapp, S., Soto, U., and Just, W. W. (1993). Import of firefly luciferase into peroxisomes of permeabilized Chinese hamster ovary cells: a model system to study peroxisomal protein import in vitro. Exp. Cell Res. 205, 59-65.

Sheikh, F. G., Pahan, K., Khan, M., Barbosa, E., and Singh, I. (1998). Abnormality in catalase import into peroxisomes leads to a severe neurological disorder. Proc. Natl. Acad. Sci. USA 95, 2961-2966.

Shimozawa, N., Zhang, Z., Suzuki, Y., Imamura, A., Tsukamoto, T., Osumi, T., Fujiki, Y., Orii, T., Barth, P. G., Wanders, R. J. A., and Kondo, N. (1999). Functional heterogeneity of C-terminal peroxisome targeting signal 1 in Pex5p-defective patients. Biochem. Biophys. Res. Commun. 262, 504-508.

Singh, I. (1996). Mammalian peroxisomes: metabolism of oxygen and reactive oxygen species. In Peroxisomes—biology and role in toxicology and disease, Reddy, J. K., Suga, T., Mannaerts, G. P., Lazarow, P. B., and Subramani, S., eds. (Annals of the New York Academy of Sciences, Volume 804, New York, N. Y.), pp. 612-627.

Smythe, E., Redelmeir, T. E., and Schmid, S. L. (1992). Receptor-mediated endocytosis in semiintact cells. Methods Enzymol. 219, 223-234.

Storrie, B., and Madden, E. A. (1990). Isolation of subcellular organelles. Methods Enzymol. 182, 203-225.

Subramani, S. (1998). Components involved in peroxisome import, biogenesis, proliferation, turnover, and movement. Physiol. Rev. 78, 171-180.

Terlecky, S. R., Legakis, J. E., Hueni, S. E., and Subramani, S. (2001). Quantitative analysis of peroxisomal protein import in vitro. Exp. Cell Res. 263, 98-106.

Terlecky, S. R., and Fransen, M. (2000). How peroxisomes arise. Traffic 1, 465-473.

Terlecky, S. R. (2002). In vitro analysis of peroxisomal protein import. In Current Protocols in Cell Biology, J. S. Bonifacino, M. Dasso, J. Lippincott-Schwartz, J. B. Hartford, and K. M. Yamada, eds. (New York, N. Y.: John Wiley & Sons, Inc.) pp. 11.15.1-11.15.10.

Walton, P. A., Wendland, M., Subramani, S., Rachubinski, R. A., and Welch, W. J. (1994). Involvement of 70 kDa heat-shock proteins in peroxisomal import. J. Cell Biol. 125, 1037-1046.

Wanders, R. J. A., Kos, M., Roest, B., Meijer, A. J., Schrakamp, G., Heymans, H. S. A., Tegelaers, W. H. H., van den Bosch, H., Schutgens, R. B. H., and Tager, J. M. (1984). Activity of peroxisomal enzymes and intracellular distribution of catalase in Zellweger syndrome. Biochem. Biophys. Res. Comm. 123, 1054-1061.

Wendland, M., and Subramani, S. (1993). Cytosol-dependent peroxisomal protein import in a permeabilized cell system. J. Cell Biol. 120, 675-685.

All the references cited above are incorporated herein by reference in their entirety, whether specifically incorporated or not. This application claims the benefit of the filing date of U.S. Provisional application Ser. No. 60/422,100, filed Oct. 30, 2002, which is incorporated by reference herein in its entirety.

Having now fully described this invention, it will be appreciated by those skilled in the art that the same can be performed within a wide range of equivalent parameters, concentrations, and conditions without departing from the spirit and scope of the invention and without undue experimentation.

We claim:

1. A modified human catalase polypeptide having a carboxy-terminal peroxisome targeting signal (PTS) that has been modified from a native sequence of Lys-Ala-Asn-Leu (SEQ ID NO: 1) by replacement of SEQ ID NO: 1 in human catalase with a PTS comprising the sequence $Xaa_{-3}Xaa_{-2}Xaa_{-1}$, wherein, independently, $Xaa_{-3}$ is Ser, Ala or Cys;

$Xaa_{-2}$ is Lys, Arg or His; and $Xaa_{-1}$ Leu or Met, and wherein the replacement sequence comprises, to the amino-terminal side of $Xaa_{-3}$, n additional amino acid residues wherein n is an integer between 2 and about 17, the additional residues being numbered sequentially from $Xaa_{-4}$ for the first additional residue to $Xaa_{-20}$ for the seventeenth additional residue.

2. The modified catalase polypeptide of claim 1, wherein n is between about 5 and about 17.

3. The modified catalase polypeptide of claim 2, wherein n is between about 7 and about 13.

4. The modified catalase polypeptide of claim 2, wherein n is between about 5 and about 2.

5. The modified catalase polypeptide of claim 2, wherein n is 9.

6. The modified catalase polypeptide of claim 1, wherein residues at any one of $Xaa_{-6}$ to $Xaa_{-4}$ are hydrophobic amino acids.

7. The modified catalase polypeptide of claim 6, wherein residues at any one of $Xaa_{-8}$ to $Xaa_{-4}$ are, independently, Leu, Val, Ile, Ala or Gly.

8. The modified catalase polypeptide of claim 1, wherein residue $Xaa_{-4}$ is a positively charged amino acid.

9. The modified catalase polypeptide of claim 8, wherein residue $Xaa_{-4}$ is Lys, Arg or His.

10. The modified catalase polypeptide of claim 9, wherein residue $Xaa_{-4}$ is Lys.

11. The modified catalase polypeptide of claim 1, wherein $Xaa_{-3}$ is Ser, $Xaa_{-2}$ is Lys, and $Xaa_{-1}$ is Leu.

12. A modified catalase polypeptide according to claim 2, wherein the four C-terminal amino acids are encoded by the coding nucleotides from a reverse primer, the sequence of which is SEQ ID NO:18.

13. The modified catalase polypeptide of claim 1, wherein, when the polypeptide is contacted with cells in vitro, it is imported into peroxisomes at a rate that exceeds the rate of import of native human catalase under the same conditions.

14. A pharmaceutical composition comprising:
(a) the modified catalase polypeptide of claim 1; and
(b) a pharmaceutically acceptable excipient or carrier.

15. A pharmaceutical composition comprising:
(a) the modified catalase polypeptide of claim 2; and
(b) a pharmaceutically acceptable excipient or carrier.

16. A pharmaceutical composition comprising:
(a) the modified catalase polypeptide of claim 13; and
(b) a pharmaceutically acceptable excipient or carrier.

17. A deliverable, peroxisomally-targeted polypeptide comprising:
(a) the modified catalase polypeptide of claim 1, and
(b) a delivery or translocation molecule or moiety bound thereto or associated therewith.

18. A deliverable, peroxisomally-targeted polypeptide comprising:
(a) the modified catalase polypeptide of claim 2, and
(b) a delivery or translocation molecule or moiety bound thereto or associated therewith.

19. The deliverable, peroxisomally targeted polypeptide of claim 17, wherein the delivery molecule is a peptide or polypeptide.

20. The deliverable polypeptide of claim 19 wherein the peptide or polypeptide is selected from the group consisting of (a) HIV-TAT protein or a translocationally active derivative thereof, (b) penetratin having the sequence RQIKIWFQNRRMKWKK (SEQ ID NO: 4), (c) a penetratin variant W48F having the sequence RQIKIFFQNRRMKWKK (SEQ ID NO: 5)

(d) a penetratin variant W56F having the sequence RQIKIWFQNRRMKFKK (SEQ ID NO: 6)

(e) a penetratin variant having the sequence RQIKIWFQNRRMKFKK (SEQ ID NO:7)

(f) herpes simplex virus protein VP22 or a translocationally-active homologue thereof from a different herpes virus; and (g) Pep-1, having the sequence KETWWETWWTEWSQPKKKRKV (SEQ ID NO:9).

21. The deliverable polypeptide of claim 17 wherein the delivery moiety associated with the modified catalase is a liposome which comprises effective concentrations of external membrane phosphatidylserine for uptake by phagocytic cells or other phosphatidylserine-recognizing cells.

22. A method for reducing the concentration of hydrogen peroxide in a cell, comprising contacting said cell with a modified catalase polypeptide of claim 1, under conditions wherein said polypeptide is targeted to peroxisomes in an amount sufficient to reduce said concentration.

23. The method of claim 22, wherein the modified catalase polypeptide further comprises a delivery or translocation molecule or moiety bound thereto or associated therewith.

24. The method of claim 22, wherein the contacting is in vitro.

25. The method of claim 22, wherein the contacting is in vivo.

26. A method for treating a mammalian subject suffering from a disease or condition associated with or caused by an inadequate level of peroxisomally active catalase, comprising administering to the subject an effective amount of the modified catalase polypeptide of claim 1.

27. A method for treating a subject suffering from a disease or condition associated with or caused by an inadequate level of peroxisomally active catalase, comprising administering to the subject an effective amount of the pharmaceutical composition of claim 14.

28. A method for treating a subject suffering from a disease or condition associated with or caused by an inadequate level of peroxisomally active catalase, comprising administering to the subject an effective amount of the pharmaceutical composition of claim 15.

29. The method of claim 26, wherein the subject is a human.

30. The method of claim 26, wherein the disease or condition is age-related.

31. The method of claim 26 wherein said administering is topical.

* * * * *

UNITED STATES PATENT AND TRADEMARK OFFICE
CERTIFICATE OF CORRECTION

| | | |
|---|---|---|
| PATENT NO. | : 7,601,366 B2 | Page 1 of 1 |
| APPLICATION NO. | : 10/533124 | |
| DATED | : October 13, 2009 | |
| INVENTOR(S) | : Terlecky et al. | |

It is certified that error appears in the above-identified patent and that said Letters Patent is hereby corrected as shown below:

On the Title page,

Item [*] Notice: Subject to any disclaimer, the term of this patent is extended or adjusted under 35 USC 154(b) by (394) days Delete the phrase "by 394 days" and insert -- by 912 days --

Signed and Sealed this

Sixth Day of April, 2010

David J. Kappos
*Director of the United States Patent and Trademark Office*